United States Patent
Wolz

(10) Patent No.: US 9,949,808 B2
(45) Date of Patent: Apr. 24, 2018

(54) PROCESS FOR THE PRODUCTION OF A CERAMIC BODY, IN PARTICULAR OF A DENTAL CERAMIC BLANK, WITH SPATIALLY SELECTIVELY ADJUSTABLE DEGREES OF PHYSICAL PROPERTIES

(71) Applicant: WDT-Wolz-Dental-Technik GmbH, Bad Sobernheim (DE)

(72) Inventor: Stefan Wolz, Bad Sobernheim (DE)

(73) Assignee: WDT-Wolz-Dental-Technik GmbH, Bad Sobernheim (DE)

( * ) Notice: Subject to any disclaimer, the term of this patent is extended or adjusted under 35 U.S.C. 154(b) by 0 days.

(21) Appl. No.: 15/364,745

(22) Filed: Nov. 30, 2016

(65) Prior Publication Data
US 2017/0189143 A1    Jul. 6, 2017

(30) Foreign Application Priority Data

Dec. 7, 2015  (DE) .......................... 10 2015 121 246
May 12, 2016  (EP) ..................................... 16169371

(51) Int. Cl.
C04B 41/00    (2006.01)
A61C 13/00    (2006.01)
(Continued)

(52) U.S. Cl.
CPC ...... *A61C 13/0022* (2013.01); *A61C 13/0004* (2013.01); *A61C 13/0006* (2013.01);
(Continued)

(58) Field of Classification Search
CPC .... C04B 41/009; A61C 13/0022; B05D 3/007
(Continued)

(56) References Cited

U.S. PATENT DOCUMENTS

2008/0241551 A1* 10/2008 Zhang .................... B82Y 30/00
                                                           428/428
2011/0183297 A1*  7/2011 Thiel ...................... A61C 13/20
                                                           433/217.1

FOREIGN PATENT DOCUMENTS

WO    WO 2014206439 A1 * 12/2014 ........... C04B 41/009

OTHER PUBLICATIONS

Liu et al. Fabricatin of coloured zirconia ceramics by infiltrating water debound injection moulded green body. Advances in Applied Ceramics 2010 pp. 1-5.*

* cited by examiner

*Primary Examiner* — Cachet I Sellman
(74) *Attorney, Agent, or Firm* — Frank H. Foster; Kremblas & Foster

(57) ABSTRACT

A process for producing a ceramic body (100), in particular a dental ceramic blank, having selectively adjustable degrees of expression of one or more different physical properties, wherein the ceramic body (100) has a porosity to enable the control of a selective distribution of one or more chemical substances (101, 102) that are suitable for influencing the physical properties of the ceramic body (100), and in a first step, which is a loading step, the ceramic body is loaded with one or more solutions (104) of the one or more chemical substances (101, 102). In a second step, which is a distribution step, the distribution of the one or more chemical substances (101, 102) within the porous ceramic body (100) is controlled, wherein a progression and/or a spatial progression of the degree of expression of the one or more physical properties can be produced. The control is effected by adjusting one or more ambient parameters (106) in an environment (108), in particular by adjusting the air humidity and/or the pressure and/or the temperature.

14 Claims, 9 Drawing Sheets

(51) Int. Cl.
  *B05D 3/00* (2006.01)
  *C03C 23/00* (2006.01)
  *C03C 19/00* (2006.01)
  *B28B 11/24* (2006.01)
  *A61C 13/083* (2006.01)
  *A61C 13/08* (2006.01)
  *A61C 13/20* (2006.01)

(52) U.S. Cl.
  CPC .......... *A61C 13/082* (2013.01); *A61C 13/083* (2013.01); *A61C 13/20* (2013.01); *B05D 3/007* (2013.01); *B28B 11/243* (2013.01); *C03C 19/00* (2013.01); *C03C 23/0095* (2013.01)

(58) Field of Classification Search
  USPC ........................................................ 427/2.26
  See application file for complete search history.

PROCESS FOR THE PRODUCTION OF A CERAMIC BODY, IN PARTICULAR OF A DENTAL CERAMIC BLANK, WITH SPATIALLY SELECTIVELY ADJUSTABLE DEGREES OF PHYSICAL PROPERTIES

BACKGROUND OF THE INVENTION

The invention relates to a process for producing a ceramic body, in particular a polychromatically, monochromatically or spatially colored dental ceramic blank, with selectively adjustable degrees of expression of one or more physical properties. The one or more physical properties preferably exhibit varying degrees of expression with respect to spatially different regions of the ceramic body, or the ceramic body exhibits a planar, i.e. two-dimensional, and/or a spatial, i.e. three-dimensional, progression of the degrees of expression of the one or more physical properties. The physical properties are understood to include, for example, optical properties, such as opacity and translucency, mechanical properties, such as hardness, (flexural) strength, and (fracture) toughness, and structural properties, such as crystal system configurations, density and/or porosity, etc.

In recent years, what is known as yttrium stabilized zirconium oxide, more particularly, partially stabilized zirconium oxide interspersed with approximately a 3% mole fraction of yttrium oxide (3Y-TZP=yttria-tetragonal zirconia polycrystals), has gained widespread use as an all-ceramic material in the field of dental technology. This is due primarily to the high mechanical stability and thermal resistance of these high-performance ceramic frameworks, but also to their outstanding biocompatibility. Coloring of all-ceramic dental prostheses is typically carried out in a final step by means of veneering, i.e. the application of an additional ceramic layer onto the dental prosthesis, such as a crown or bridge, which has already been shaped through milling. These additional ceramic layers, which possesses outstanding coloring and shaping possibilities, are still being applied by hand on an individual basis, and with great effort, to each individual dental prosthesis. However, studies have shown that the chipping rate of this aesthetic ceramic veneer is five times as great as that of established metallic ceramic veneering systems (VMK). Complaints associated with aesthetic ceramic veneers, along with high manufacturing costs, make it desirable to dispense with these veneers. However, without ceramic veneers, the hardness of yttrium-stabilized zirconium oxide full ceramics is twice as high as that of a natural tooth crown, which leads to a wearing down of opposing and neighboring teeth and thus to damage of the remaining dentition.

Another problem that results when a ceramic veneer is dispensed with is the optical or aesthetic appearance of the dental prosthesis. It should be noted here that no unicolored tooth exists in the mouth of any patient. In a natural tooth, the darker dentine core is covered by ever-thickening layers of cutting edge mass. This leads to varying coloration and light transmission properties of the natural tooth, all the way to the virtually transparent cutting edges. A traditional, non-veneered ceramic dental prosthesis, in particular one made of pure 3Y-TZP, exhibits a spatially uniform expression of color and physical properties, in particular of hardness, but also of light transmission properties such as translucency or opacity.

To enable a crown or, alternatively, the dental prosthesis to function on an aesthetic level, the following features must be considered and implemented. To begin with, the layer of dentine must have the basic tooth color of the patient. The dentine color and the thickness of the cutting edge layer create the actual tooth color of the patient. The natural tooth develops the three-dimensional color combination during growth and through later wear and tear. In addition, there is an ever-lightening color progression starting from the dentine core all the way to the cutting edge. The dental enamel may also exhibit lighter and/or transparent areas. Furthermore, in older patients the darker dentine-colored edges of crowns are clearly visible, and therefore the new dental prostheses must be adapted accordingly.

Various processes for coloring dental prostheses with metallic ions and/or metal complexing solutions and gels are known from WO 2008 098 157, WO 2013 055 432, WO 0046 168, WO 2004 110 959, DE 199 04 522 B4, DE 10 2008 026 980 A1, WO 00/46168 A1, WO 2011/156602 A2 or DE 20 2011 109 956 U1, WO 11 15 66 02, EP 2013 06 31 20, and US 2011 039 805. However, at most a simple and unicolored coloration of a dental prosthesis can be achieved through immersion or spraying. Although attempts have been made to achieve tooth color structures or similar colorations of a dental prosthesis using brushes or by applying drops, it is nevertheless impossible to achieve natural-looking results with known fluids or with known solutions or gels, and as a result, noticeable color differences persist between natural teeth and dental prostheses.

To be able to produce dental prostheses in an automated process, rather than producing them manually on an individualized basis, it would be necessary, for example, to produce a multitude of very different ceramic blanks with spatial color progressions but also with spatial progressions of physical properties, if economical and aesthetic results are to be achieved.

The patents EP 202 4300, WO 2014 062 375, WO 02 09 6 12, U.S. Pat. No. 9,212,065 B2, DE 2020 090 187 24, EP 235 97 71 and EP 185 97 57 teach the coloring of the starting material, in particular of powders or pastes. The powders or pastes are then poured or applied in layers, with each layer exhibiting a specific color. Thus 7-10 layers are required in order to achieve a two-dimensional coloring or alternatively to achieve a two-dimensional or planar color progression.

A process for producing a ceramic dental prosthesis with improved optical translucency is known from US 2011 269 618. The starting material, tetragonal polycrystalline zirconium powder, is developed for this purpose with a particularly small particle size. Due to the smaller particle size, the dental prosthesis that is pressed from the material has a lower refractive index and therefore increased translucency. According to US 2013 022 15 54 A1, it is possible to achieve at least a roughly graduated progression of optical physical properties such as opacity and/or translucency, in a manner that is similar to the coloring of dental ceramic blanks, through the layered pouring of various ceramic dental powders that have varying yttrium content. The pressed dental ceramic blank then exhibits a roughly graduated two-dimensional progression of opacity, which corresponds to the number and the thickness of the layers.

One disadvantage of the aforementioned processes is that only a planar, i.e. a two-dimensional color progression and/or progression of the degree of translucency can be achieved in the manner described. Beyond this, the creation of each additional gradation of the color progression and/or progression of expression requires an additional process step. The production of a three-dimensional or spatially as well as finely graduated progression would require the pouring of a multitude of powder layers not only on top of one another but also side by side, which would be beyond the scope of the process described and which would lead to disproportionate additional costs. Amongst other things, it would be necessary to store, test and inspect hundreds of different powders with different physical properties and colorings.

A complicated sol-gel process for producing a millable dental ceramic blank with geometrically defined areas of differentially expressed translucency is known from US 2015 028 2905 A1. In the same, a first zirconium solution is cast into a mold and is cured to form a first zirconium gel. The first zirconium gel is placed in a second, larger mold and is overmolded by a second zirconium solution. The process is then repeated until the desired number of zirconium gel layers is achieved. The layered zirconium gel body is subsequently sintered, to obtain a millable dental ceramic blank. In this way, each zirconium layer can exhibit a different translucency. While it is true that the described process can also be used to achieve spatially differentiated degrees of translucency within the dental ceramic blank, each additional region nonetheless requires an additional process step that involves casting the zirconium solution and then curing the solution to form the zirconium gel, as a result of which the process is exceptionally time-consuming and would thus be uneconomical.

SUMMARY OF THE INVENTION

The object of the invention is therefore to provide an improved process, which can be automated and is therefore more affordable, for producing a ceramic body, in particular a dental ceramic blank, which has a progression and/or spatial progression of the degrees of expression of one or more physical properties. In particular, it is the object of the invention to employ such a process for the simultaneous adjustment of a monochromatic, polychromatic and or spatially polychromatic color progression.

The object is achieved by a process according to claim 1 and by a ceramic blank that is produced in particular using a process according to the invention.

Advantageous, optional embodiments and/or refinements arise wholly or partially from the dependent claims.

A process according to the invention of the type described in the introductory part is characterized by the fact that the ceramic body has a porosity for the purpose of controlling a selective distribution of one or more chemical substances that are suitable for influencing the physical properties of the ceramic body. In the field of dental technology, in particular, a porous ceramic is generally understood as a porous ceramic body that is formed, for example, by pressing ceramic powder, by slip casting from ceramic slurry, by means of a 3-D ceramic printer, or by means of similar suitable processes. In particular, the porous ceramic body is a dental ceramic blank, for example, a fired porous ceramic white or a porous pressed glass ceramic. Such a dental ceramic blank can be used as a green body for a process according to the invention. In a first step, which is a loading step, the porous ceramic body is loaded with one or more solutions of the one or more chemical substances. Loading is generally understood as the addition of coloring pigments to the porous ceramic body, preferably to the top surface of the porous ceramic body. Loading can be accomplished, in particular, by applying the chemical substances, which are preferably contained in a solution, using a brush or some other suitable application tool, but also by spraying the porous ceramic body or by simply immersing the porous ceramic body in a solution of the chemical substances. To load the porous ceramic body with the chemical substances, for example yttrium oxide, cerium oxide or any other organic and/or inorganic pure substances and mixtures of substances that are suitable for influencing the physical properties of the ceramic body, and to distribute the same in a selective manner within the porous ceramic body, the chemical substances are contained in a liquid, in particular an aqueous solution. In a second step, which is a distribution control step, the distribution of the one or more chemical substances within the porous ceramic body is controlled. That is to say, the movement of the chemical substances is controlled in such a way that they are transported to any selectable positions within the porous ceramic body, so as to establish a planar or two-dimensional progression and/or a spatial or three-dimensional progression of the degrees of expression of the one or more physical properties. For this purpose, one or more ambient parameters, in particular the air humidity and/or pressure and/or temperature in an environment that forms a closed system, for example a sealed vessel, cabinet, room or the like, in which the porous ceramic body is located, are adjusted. An adjustment in this context is understood not solely as a quantitative adjustment but also as an adjustment with respect to defined, localized areas within the environment, in other words, different surfaces and/or surface areas of the porous ceramic may be acted on by one or more ambient parameters.

In one advantageous process variant, the one or more chemical substances are distributed within the porous ceramic body by means of a convection flow. In this case, a flow direction and flow rate, preferably of the chemical substances in solution, are controlled within the environment by the selective generation of ambient parameter gradients. In particular, adjustments are made to differences in air humidity and/or differences in pressure and/or differences in temperature with respect to various surfaces and/or with respect to various surface areas of the porous ceramic.

According to an advantageous embodiment of the process, the speed of movement of the one or more chemical substances and/or the flow rate, in particular of the chemical substances in solution, is controlled by increasing and/or decreasing one or more of the ambient parameter gradients. For example, a first ambient pressure that is acting on a first surface of the porous ceramic may be increased, and a second ambient pressure that is acting on a second surface of the porous ceramic, opposite the first surface, may be decreased or maintained, thereby increasing the amount of the pressure gradient with respect to the two surfaces. This in turn leads to a change, in particular to an increase in the speed of movement and/or the flow rate.

According to a likewise advantageous embodiment of the process, the direction of movement of the one or more chemical substances and/or the direction of flow, in particular of the chemical substances in solution, is controlled by changing the direction of one or more of the ambient parameter gradients. For example, the first ambient pressure may be applied to a first surface of the porous ceramic body and the second ambient pressure may be applied to another, third surface of the porous ceramic body, thereby controlling the direction of movement and/or a direction of flow between the first and third surfaces of the porous ceramic body. The direction of movement and/or the direction of flow between, for example, the first and the second surface or between the first and the third surface can be reversed by reversing the progression of the ambient parameter gradients (i.e. by changing the sign of the gradient).

In an optional process variant, at least one surface or at least one portion of a surface of the porous ceramic body is isolated and/or sealed off from the environment during the loading step and/or during the distribution control step. At least one other surface or at least one other portion of a surface of the porous ceramic body is freely accessible for loading and/or for control, i.e. it is in contact with the environment. In this way, ambient parameters can be adjusted in a localized manner with respect to defined surfaces and/or partial regions of surfaces. The isolation and/or sealing off may be employed during the loading step to enable the locally selective loading of the porous ceramic body with the one or more chemical substances and/or the chemical substances in solution, and during the distribution control step for the selective control of the distribution, in particular for the selective control of the direction of movement and/or the direction of flow.

Advantageously, the porous ceramic body is loaded with the one or more chemical substances and/or the chemical substances in solution via the at least one freely accessible surface.

According to an optional process variant, the freely accessible surface of the porous ceramic body is partially isolated and/or sealed off prior to being loaded with the one or more chemical substances and/or the chemical substances in solution, so that portions of this surface or these surface areas are inaccessible for loading with the one or more chemical substances and/or the chemical substances in solution and/or for the action of ambient parameters. Advantageously, the freely accessible surface is directed downward, in the direction of gravity, for loading with the one or more chemical substances and/or the chemical substances in solution.

Optionally, the at least one freely accessible surface of the porous ceramic body may be in contact with the surrounding environment during the distribution control step. This allows the freely accessible surface to be acted on by one or more of the ambient parameters. Likewise during the distribution control step, the at least one isolated and/or sealed off surface can be sealed off and/or isolated from one or more of the ambient parameters. This enables individual areas of the porous ceramic body to be acted on in a selective manner by ambient parameters, allowing the direction and the degree of expression of the ambient parameter gradients to be selectively adjusted in order to control the spatial distribution of the one or more chemical substances within the porous ceramic body. Advantageously, the sealing off and/or isolation is carried out by means of a mold, a housing, or the like, and/or a film and/or a coating. In the case of a mold, this may be a silicone mold, in the case of a film, it may be a self-adhesive film and in the case of a coating, it may be a silicone, latex, and/or wax coating, for example.

In one exemplary process variant, the porous ceramic body is sealed off and/or isolated by inserting it in a precise fit into a mold, in particular into a partially open silicone mold, with the pressure inside the mold being lower than the ambient pressure, for example. In one embodiment example of the process, at least a first surface and/or a first partial surface area of the porous ceramic body is located inside the mold, with this first surface and/or this first partial surface area being isolated and/or sealed off at least with respect to one ambient parameter, for example with respect to the air humidity, or the pressure, that is present in the environment. At least a second surface and/or a second partial surface area is located outside of the mold, with this second surface and/or this second partial surface area being freely accessible with respect to the ambient parameters. At least a third surface and/or a third partial surface area is located inside the mold and lies in a precise fit against an interior wall of the mold in such a way that a negative or positive pressure in relation to the ambient pressure may be adjusted inside the mold. For example, a pressure difference can be established between the first surface of the porous ceramic body lying on the inside and the second surface thereof lying on the outside, in which case the pressure inside the mold is lower than the ambient pressure. To reverse the direction of the pressure gradient, the pressure inside the mold may be increased, or alternatively, the ambient pressure may be decreased, until the pressure inside the mold is higher than the ambient pressure acting on the second, freely accessible surface. Alternatively, the porous ceramic body can be used to reverse the direction of the pressure gradient inside the mold, such that the first surface is located, freely accessible, outside the mold and the second surface is located, isolated and/or sealed off, inside the mold. Optionally, the porous ceramic body may be acted on by additional ambient parameter gradients, such as differences in air humidity, in which case the air humidity acting on the second freely accessible surface is preferably adjusted. By using self-adhesive film on the second freely accessible surface, an ambient parameter such as air humidity can be adjusted with respect to individual second surface areas.

Optionally, the porous ceramic body may be loaded with the one or more chemical substances and/or the chemical substances in solution by means of a loading body. The loading body comprises, in particular, a porous and/or sponge-like material that facilitates the absorption of the one or more chemical substances and/or the chemical substances in solution. The loading body is then laced, more particularly saturated, with a solvent and with the chemical substances contained therein. During the loading step, in order to load the porous ceramic body with the one or more chemical substances and/or the chemical substances in solution, the ceramic body is placed with its freely accessible surface on the loading body. This optional loading method offers the advantage that the entire freely accessible surface of the porous ceramic body is in physical contact with the loading body, allowing the chemical substances to act uniformly on said surface. The concentration of the one or more chemical substances that is/are supplied to the porous ceramic body during the loading step can thereby be kept constant over the entire freely accessible surface.

The loading body can comprise one or more layers, for example, with the one or more layers containing the same chemical substance for adjusting the progression and/or the spatial progression of the degree of expression of an individual physical property within the porous ceramic body. To adjust a progression and/or a spatial progression of the degrees of expression of different physical properties within the porous ceramic body, different layers may be laced and/or saturated with different chemical substances or solutions thereof. The multiple layers of the loading body may be arranged horizontally, side by side and/or vertically, one below the other or one on top of the other. A vertical progression of the degree of expression within the porous ceramic body is facilitated or produced by vertically arranged layers. The porous ceramic body that is to be loaded is in contact with only the uppermost layer of the loading body, or lies on the uppermost layer of the loading body. The chemical substances or the solutions thereof, which are contained in the remaining layers, each pass through the layers located above them in each case before penetrating into the porous ceramic body. In this way, a time-staggered loading with different chemical substances can be achieved, which results in a progression of the degrees of expression. A horizontal arrangement of the layers can facilitate or produce a horizontal progression of the degrees of expression within the porous ceramic body during the loading of the porous, ceramic body. In this case, the porous ceramic body that is to be loaded is in contact with all of the layers that are arranged horizontally side by side, or lies on top of these, so that the chemical substances of the individual layers penetrate into the porous ceramic body at the same time, but in different partial surface areas of the freely accessible surface. A combination of layers arranged vertically, above or below one another and horizontally, side by side facilitates or produces a three-dimensional or spatial progression of the degrees of expression of one or more physical properties within the porous ceramic body during loading. Depending on the desired end result, any desired combination of layers horizontally, side by side, and vertically, one above the other or one below the other may be produced. Naturally, different chemical substances may also be added in sequence to the porous ceramic body, in multiple loading steps, each involving a single layer of the loading body, in order to produce a ceramic body that features progressions of the degrees of expression of different physical properties. This method is particularly advantageous when combined with a 3-D printed ceramic structure. In contrast to a pressed ceramic blank, the printed ceramic structure features a markedly higher porosity or a markedly lower density, which makes further processing, for example using a ceramic mill, more difficult. Through multiple loading steps in sequence, the density of a printed ceramic structure can be increased, for example, from 0.8 g/mm$^3$ to 3.5 g/mm$^3$, by filling the pores or the porosity of the ceramic structure with the chemical substances.

According to an optional process variant, the loading body comprises a filter. The filter preferably forms the uppermost layer of the loading body and can be laced or saturated with a solution, without the addition of chemical substances that are suitable for influencing physical properties. By using a filter that is made, in particular, of the same or a similar material as is found in the other layers of the loading body, a more uniform distribution of the chemical substances during the loading step can be achieved, thereby facilitating the control of the progression of the degrees of expression. In particular, the filter contains a solvent that is laced with zirconium nitrate.

Advantageously, the porous ceramic body is dried, and more particularly is fully dried during the distribution control step. For example, the ambient parameters, in particular the air humidity and/or the pressure and/or the temperature, may be adjusted for controlling the drying process, allowing both the drying time and the localized drying progression to be selectively varied. For instance, one, multiple, or all of the freely accessible surfaces of the porous ceramic body outward may be dried. In particular, the chemical substances may be fixed in the desired position within the porous ceramic body by drying, i.e. by evaporation of the solvent.

In accordance with an exemplary process sequence according to the invention, in a first step, for example, a planar and/or plate-shaped, porous ceramic blank and/or a ceramic framework or a porous ceramic structure, in particular a white, which is suitable for use in the field of dentistry, is prepared. Plate-shaped dental ceramic blanks are commercially available and are suitable for processing using traditional CAD/CAM ceramic milling machines and for subsequent final sintering, to produce a ready-made dental prosthesis. In a second process step, one or more surfaces of the ceramic blank are provided with isolation and/or sealing off, for which purpose the ceramic blank is placed in a waterproof and air impermeable, i.e. sealing mold, in particular a silicone mold. In this step, at least one surface or one partial surface area of the ceramic blank is not isolated and/or sealed off by the mold, leaving this surface freely accessible for the action of ambient parameters or for loading. In a third step, a loading step, the freely accessible surface or the freely accessible surface area of the ceramic blank is loaded with one or more chemical substances that are suitable for influencing the physical properties of the ceramic blank, with the chemical substances, for example cerium, yttrium, calcium and/or magnesium, being contained in a liquid, in particular an aqueous solution, or being present in the form of a solution. In a fourth step, the ceramic blank is placed within an environment, the ambient parameters of which, in particular the air humidity and/or pressure and/or temperature, are adjustable. This environment may, for example, be a climatic chamber or a compartment dryer, but may also be an accessible room, the ambient parameters of which are adjustable. In this case, the ceramic blank may be left in the mold in such a way that only the freely accessible surface is in contact with the environment. In a fifth step, which is a distribution control step, the distribution of the chemical substances that were introduced into the ceramic blank by means of loading is controlled. For this purpose, at least one ambient parameter, in particular the air humidity and/or the pressure and/or the temperature, is adjusted to create an ambient parameter gradient between the one or more freely accessible surfaces and the one or more isolated and/or sealed off surfaces of the ceramic blank.

Alternatively or optionally, in an additional drying step that follows the distribution control step or the distribution of the chemical substances within the porous ceramic body, the porous ceramic body, or the ceramic blank, can be heat treated. In this step, the porous ceramic body or the ceramic blank is exposed to a temperature ranging from 80° C. to 1200° C., preferably from 80° C. to 800° C., for the formation of an oxide phase, in particular a nitrate oxide phase. Cations, for example of salts, that are in solution and are added to the solvent as chemical substances for influencing physical properties, can react with oxygen to form oxides or an oxide phase. The porous ceramic body is subjected to heat treatment in particular to facilitate both a localized fixation and a development of physical properties. By adding zirconium nitrate to the solvent or to the chemical substances in solution, and by applying a drying step involving heat treatment, the chemical substances used for adjusting the physical properties of the porous ceramic body can be reliably fixed in the desired position. The heat treatment causes the zirconium nitrate to form a fixed structure within the pores of the porous ceramic, which traps or fixes the chemical substances. In particular, the heat treatment enables milling using water-cooling CAD/CAM machinery, without fear of the chemical substances becoming delocalized or displaced within the porous ceramic. Depending on the ceramic that is used, temperatures of, for example, 700° C.-2000° C. are established in an air or inert gas atmosphere (for example nitrogen, argon . . . ) at ambient pressure or in a vacuum, and the ceramic is exposed to these conditions until a density of approximately 94% to approximately 100% of the final density, i.e. the density after the final sintering, is achieved.

According to an optional process variant, a CTE [coefficient of thermal expansion] equalization may be carried out during and/or after the distribution of the chemical substances within the porous ceramic body, by loading the porous ceramic body at least partially with an equalizing substance. To finish a dental prosthesis, the ceramic blank is generally subjected to a final sintering process, i.e. a high temperature treatment, whereby the material is sealed and the pore spaces are filled. Due to the varying thermal expansion coefficients (CTE) of the various materials, for example of the ceramic blank and of the infiltrated chemical substances, the different volume expansions that are induced by this heat can produce stresses. Stresses of this type frequently lead to the creation of fissures, making the ceramic body unusable as a dental prosthesis. The addition of an equalizing substance allows the varying thermal expansion coefficient values to be equalized, thereby preventing these stresses as well as the creation of fissures.

In an additional optional process step, following the distribution and optionally the fixation of the chemical substances, the porous ceramic body or the ceramic blank can be milled into the desired shape, in particular into the shape of a dental prosthesis, using a CAD/CAM milling machine. In a further additional optional process step, following the distribution and optionally the fixation of the chemical substances, and preferably following a shaping process, for example by milling, the porous ceramic body or the ceramic blank may be sintered or may be subjected to final sintering. In this step the pores are closed, thereby fixing the chemical substances in such a way that a progression of one or more physical properties that corresponds to the distribution results. In particular, prior to the distribution of the chemical substances, the ceramic blank may be presintered at a lower temperature, and once the chemical substances have been distributed, the ceramic blank can be subjected to a final sintering at a higher temperature.

According to an optional process variant, the one or more solutions of one or more chemical substances are controlled within the porous ceramic body in such a way that differences in the concentration of the dissolved chemical substances are adjusted within the various regions of the porous ceramic body. The varying concentration leads to a varying degree of expression of the physical properties. The density of the porous ceramic body can be selectively adjusted spatially by adjusting varying concentrations of the chemical substances that are contained in the solution. Once the solvent has been dried or evaporated, the chemical substances remain within the pores and produce a localized increase in density.

The solution with which the porous ceramic body is loaded, or the distribution of which within the porous ceramic body is controlled, preferably contains distilled water, zirconium nitrate, and at least one chemical substance that is suitable for influencing the physical properties of the porous ceramic body. In particular, a degree of expression of the opacity and/or translucency of the porous ceramic body can be controlled by means of a solution containing yttrium. The yttrium is preferably added in the form of yttrium nitrate or yttrium chloride. A degree of expression of a hardness and/or toughness and/or strength of the porous ceramic body can be controlled, in particular, by means of a solution containing cerium. The cerium is preferably added to the solution in the form of cerium nitrate or cerium chloride.

According to an advantageous process variant, a configuration of a crystal system of the porous ceramic body or of individual regions of the porous ceramic body can be controlled by means of a solution containing calcium and/or magnesium and/or yttrium. To at least locally stabilize the crystal system of the porous ceramic body in a cubic configuration, a mole fraction of at least 16% calcium and/or 16% magnesium and/or 8% yttrium may be added to the solution. To at least locally stabilize the crystal system of the porous ceramic body in a tetragonal configuration, a mole fraction of at least 8% calcium and/or 8% magnesium and/or 4% yttrium may be added to the solution. The crystalline configuration of the porous ceramic body has a significant impact on its physical properties, and the physical properties of the porous ceramic body are indirectly adjusted by controlling the distribution of chemical substances that are suitable for influencing the configuration of the crystal system.

In an optional, advantageous process variant, a crystal system is stabilized within pores of the porous ceramic body by means of a solution, in particular an aqueous solution, which contains zirconium nitrate along with calcium and/or magnesium and/or yttrium. The crystal system is stabilized in a cubic or a tetragonal configuration depending on the mole fraction of the calcium and/or the magnesium and/or the yttrium (see above). The porous ceramic body is preferably loaded with the solution in such a way, or the distribution of the solution within the pores of the porous ceramic body is controlled in such a way, that the pores can be completely or locally filled with a crystal system in a tetragonal and/or a cubic configuration.

The above-described inventive process can be additionally or alternatively used for the monochromatic, polychromatic or spatially polychromatic coloring of a porous ceramic body by loading said ceramic body with additional coloring pigments, for example, in the form of metal oxides. In addition to the chemical substances in solution, the porous ceramic body is loaded with one or more coloring pigment solutions, in particular metal oxide solutions. The distribution of these within the porous ceramic body is then controlled. The coloring pigments can optionally also be added directly to the solutions of the chemical substances that are suitable for influencing the physical properties of the porous ceramic body.

The object of the invention is further achieved by a ceramic blank that is suitable for producing dental prostheses by means of a CAD/CAM milling machine, and is produced, in particular, by a process according to the invention. A spatial distribution of one or more chemical substances that are suitable for influencing the physical properties of the ceramic blank can be controlled within the ceramic blank by means of ambient parameter gradients. After a sintering treatment, in particular a final sintering at high temperature or a heat treatment at a lower temperature, the ceramic blank exhibits a gradual and/or graduated, preferably spatial progression of the degree of expression of one or more physical properties.

The following table contains exemplary values or exemplary ranges of values for the physical properties that can be spatially selectively adjusted in regions of the ceramic body by means of the inventive process. Each of the values relates to a ceramic body that has been subjected to final sintering, i.e. a densely sintered ceramic body:

| Zirconium oxide ceramic | | | | | |
| --- | --- | --- | --- | --- | --- |
| Composition | % | 70 to 99 $ZrCO_2$ | | | |
| Density | g/cm$^3$ | 5.0 to 6.5 | DIN | EN | 623-2 |
| Open porosity | % | 0 | | | |
| Particle size (mli) | µm | 0.01 to 35 | DIN | EN | 623-3 |
| Vickers hardness | Hv | 350 to 1500 | DIN | EN | 843-4 |
| Flexural strength (3 points) | MPa | 500 to 2500 | DIN | EN | 843-1 |
| Modulus of elasticity | GPa | 150 to 250 | DIN | EN | 843-2 |
| Fracture toughness | MPa/m$^2$ | 4 to 16 | | | |

| Zirconium oxide ceramic | | | | | |
|---|---|---|---|---|---|
| Chemical solubility | μm/cm² | 1 to 250 | EN | ISO | 6872 |
| Thermal expansion (20-600° C. | 10⁻⁶/K | 8 to 12 | DIN | EN | 821 |
| Sinter shrinkage | % | 0 to 35 | | | |

| Possible processes for producing ceramic blanks | |
|---|---|
| Isostatic pressing | usable for process according to invention |
| Compression molding | usable for process according to invention |
| Slip casting | usable for process according to invention |
| HIP | usable for process according to invention |
| 3-D printing | usable for process according to invention |

Likewise part of the concept of the invention is a device for loading a porous ceramic body, in particular a dental ceramic blank, with a solution of chemical substances that is suitable for influencing the physical properties of the porous ceramic body. The loading device comprises a porous and/or sponge-like material that can be laced, preferably saturated, with the solution, such that the solution can be delivered to the porous ceramic body that is resting on the loading device, for example, or such that the porous ceramic body can be loaded with the solution. According to an advantageous embodiment, the loading device comprises at least two layers, with at least one layer being designed as a filter, that is to say, in particular, it is not laced with chemical substances used for influencing the physical properties, and/or with at least two layers each being laced with different chemical substances for influencing different physical properties.

A further part of the general inventive concept is a device for controlling the selective distribution of chemical substances within a porous ceramic body, in particular a dental ceramic blank. The chemical substances are suitable for influencing physical properties of the porous ceramic body. The control device is suitable for isolating and/or sealing off at least one surface and/or at least one part of a surface of the porous ceramic body, with at least one other surface and/or at least one other part of a surface remaining freely accessible to be acted on by adjustable ambient parameters. The device may be an open mold, for example, in particular a silicone mold, which is designed to hold the porous ceramic body in a precise fit, in such a way that the porous ceramic body is held by the silicone mold in a form-fitting manner, with one surface of the porous ceramic body remaining freely accessible.

Further exemplary features, combinations of features and embodiments within the scope of the invention will be evident from the following sections.

The process according to the invention for coloring and/or for adjusting physical properties, in particular for producing a monochromatically, polychromatically or spatially polychromatically colored dental blank with zones of adjustable physical properties in full ceramic, does not require powder mixtures or pastes, or complex layerings/pourings and/or exchangeable tanks of the 3-D printer and/or special tools. The process is based upon distribution control steps that can best be explained by known convection flow. The process comprises loading the porosities of a prefabricated ceramic blank, which is suitable in particular for dental technology, with complex pigments and/or stabilizing solutions, and then creating ambient parameter gradients. The described disadvantages of the state of the art are avoided, and a market-ready ceramic blank from a warehouse stock is colored as desired. Spatial zones are advantageously doped and adjusted by loading with combinations of zirconium stabilizers. US 2015 028 2905 and US 2011 269 618 teach complex processes for producing an improved zirconium powder. These teachings result in an increase in the cost of the powders. Surprisingly, it is possible according to the invention to produce a ceramic blank of high porosity from easily produced, cost-efficient powders. Said blank is loaded in a loading step and a distribution control step with a salt solution, which leads to crystallization in the porosities. Heat treatment produces a crystalline oxide phase transformation. The oxidation then results in oxides that precipitate in the corresponding porosities, where they adapt to space conditions. The blank thus obtains a white blank density that cannot be achieved merely by compression molding and/or by isostatic pressing and/or hot isostatic pressing. The white blank density can be twice as high, without the use of complex powder production methods and without the use of complex layering with pressing processes. The zones having different physical properties, which are adjustable according to the invention, can also be achieved in this manner, which is particularly important for porous ceramic structures when a 3-D ceramic printing process is used. Thus the process according to the invention for producing a polychromatically and/or spatially polychromatically and/or monochromatically colored dental blank that has adjustable zones of different physical properties is characterized by the presence of a partially or fully stabilized oxide in a first ceramic framework with a cubic or tetragonal or monoclinic zirconium. In a second step, a further cubic or tetragonal and/or monolithic partially or fully stabilized doped zirconium oxide is produced in the porosities. Thus at least one second crystal lattice is introduced into the first crystal lattice, the zirconium oxide lattice. The second crystal lattice may be distributed in a homogeneous or highly concentrated manner. In this way, the fracture toughness can be increased and/or the hardness reduced. This also contributes to a reduction in the cost of dental practices, since a soft material can be ground off much more quickly (costly work performed by the dentist of fitting a prosthesis into the mouth).

The ability to adjust spatial zones or regions with varying physical properties and or varying degrees of physical properties is advantageous because a high Vickers hardness, flexural strength and fracture toughness are not spatially divisible in a single-phase body. Surprisingly, however, according to the invention it is possible to introduce multiple zones or regions that have different physical properties into one ceramic body. This offers the advantage of reducing the costs associated with the complex machining of a finalized sintered zirconium ceramic by 30-50%. The finalized sintered zirconium oxide is a high-performance ceramic with a flexural strength of about 1100 MPa. Dental materials that are used to make bridges require a flexural strength of at least 500 MPa. ZrO2 (zirconium oxide) belongs to the group of oxide ceramics, and is thus an organic non-metallic material. It is also referred to as "ceramic steel". Its flexural strength is more than twice as high as that of Empress and nearly twice as high as that of infiltrated aluminum oxide ceramics (for example, InCeram Alumina). Its fracture toughness has similar characteristics. Its fatigue behavior also exceeds that of glass-infiltrated ceramics by a factor of three. Zirconium oxide ceramic is usually tetragonal polycrystalline zirconium oxide (Y-TZP=yttria-tetragonal zirconia polycrystals) partially stabilized with yttrium oxide (addition of approximately 3 mol-%). This stabilization is referred to as transition enhancement and brings about a certain inhibition of fissuring. Tensile stress acting on the tip of a fissure will induce a transformation of the metastable tetragonal zirconium oxide into the thermodynamically more advantageous monoclinical form. This transformation is associated with a local increase in volume. Compressive stress is therefore generated in a localized manner at the tip of a fissure, counteracting the external load acting from the outside on the tip of the fissure. This leads to high initial strengths and resistance to fissure, and when combined with a low susceptibility to stress corrosion, results in an outstanding lifespan for zirconium oxide frameworks. The composition of the yttrium stabilized zirconium oxide ceramic is as follows: zirconium oxide, hafnium dioxide and yttrium oxide together >99.0%; aluminum oxide and other oxides, each <0.5%. Zirconium is a metal of the titanium group. Zirconium oxide belongs to the group of oxide ceramics. Immediately after sintering, polycrystalline oxide ceramics form a dense single-phase oxide ceramic. However, these physical properties can be improved and spatially adjusted according to the invention. Zirconium oxide is produced, for example, by the chemical treatment of zircon sand (chemical composition ZrSiO4). After chemical dissolution and purification, a highly pure raw material is obtained, which is later doped with yttrium oxide (Y2O3), heat treated and ultimately ground. The resulting zirconium oxide is virtually free of any undesirable impurities. It is subsequently pressed into blocks of varying sizes (blanks). In this so-called "soft" state, it can be easily machined. This "white" is, for example, the starting blank that is used in the process according to the invention.

In the proposed process for coloring and adjusting physical properties of bound and/or unbound and/or sintered and/or continuously porous ceramic, in particular of porous bodies that are used, in particular, in dental technology, color-producing components and/or stabilizers are distributed in a ceramic body and/or in market-ready ceramic blanks. To control the direction of movement of the coloring pigments and/or the stabilizer solutions within a dense housing, e.g. made of silicone, a space that is with or without spherical pressure and has loading body materials is located within the housing to effect the airless, continuous filling of the porosities. A means for sealing and/or isolating the housing is understood as any material that is capable of encompassing the surfaces of a porous ceramic blank in a tightly sealed or air-impermeable manner. Preferably, one surface of the porous ceramic blank is placed on a capillary pressure-retaining loading body, in which or on which coloring pigment solution and/or stabilizer solutions are stored. For airless transport, the loading body is advantageously produced from loading body materials, such as microfibers, sponges, cellulose, etc. The term "loading body material" is therefore understood to include all materials or substances that are water-permeable and/or are able to store the same. The loading body materials fulfill an important purpose. The capillary force of the porous, isostatically pressed white is so strong that, for example, our tongues will immediately adhere to the porous ceramic. This is due to the high density of the porous ceramic of 0.5 g/cm$^3$ to 4.0 g/cm$^3$. If liquid is applied to the porous ceramic, e.g. using a brush, the liquid will be immediately sucked away, however the color-producing components will be sucked away more slowly than the solvent liquid. Thus the porous ceramic acts as a filter, in which the color-producing components become concentrated somewhere in the manner of a blockage. The distribution control step is able to dissolve these blockages and redistribute them within the ceramic block. However, this may mean multiple days of storage in the silicone housing under corresponding ambient parameters. For this reason, a loading body material that acts as a liquid hemming agent is selected, based upon the porosity of the ceramic blank. This results in substantially fewer undesirable concentration accumulations. This allows the color-producing components to achieve a desired coloring distribution more quickly by way of the distribution control step. Moreover, the various color-producing components and/or stabilizers are able to build up in layers in the assigned volumes, that is to say, a total volume of 50 mL for the existing ceramic porosities can be introduced in 10 mL each of different loading body materials. At a constant capillary pressure, it is then possible to place five different color component solutions and/or stabilizer solutions on top of one another and store these, without these intermixing, which is otherwise virtually impossible in a liquid. The capillary pressure-retaining loading body thus effects loading by capillary suction, inasmuch as one color-producing solution passes the pressure on to the others, thereby creating color transitions in the desired zones of the ceramic blank. The blank may also be loaded only with stabilizing complexes, with or without pressure. This means that the loading body materials take up the desired capillary pressure in the case of a moist and/or a wet substrate. Color-producing components for salts include, e.g.: sinite nitrate nanohydrates, oxyhydrate nitrates, tetrahydrate nitrates, pentahydrate nitrates, hexahydrate nitrates, chlorides, acetates, niobates, metavanadates or sulfides etc. In general, the appropriate solutions can be easily prepared by dissolving a corresponding metallic salt, for example, in the appropriate solvent, preferably water. In the case of the invention, the corresponding salts are preferably chlorates, sulfates, carbonates or in particular nitrates of the respective metal, which comprise the rare earth elements, and also, in particular, the group of lanthanides, as is well known. In the case of the sub-group elements, the transitional metals are highlighted in particular, along with sub-groups and main groups I-VIII according to the newer nomenclature of the Periodic Table of Elements. The term "solution" is well known to a person skilled in the art and should be understood in the broadest possible sense here. Of course, the metal ions or metal complexes are prepared according to the invention in a form in which they can most readily penetrate into the porous ceramic material. This will generally be a (liquid) solution or a homogeneous mixture of a corresponding solid material for loading the porosities of the ceramic body. In this case, therefore, this will generally be a (liquid) solution or a homogeneous mixture of a corresponding solid substance for loading the porosities of the ceramic body. Once the nitrates have dried, a crystal develops in the porosities. A separate heat treatment can also cause the crystal development to pass through oxidation stages. A second doping with additional stabilizers can thus be calcined onto the stabilized zircon powder of the blank. In the process according to the invention, suspensions or more particularly solutions that contain metal ions or metal complexes containing at least one element of the elements listed below are preferably used:

1. $Fe(No_3)_3 \cdot 9\ H_2O$
2. $Cr((No_3)_3 \cdot 9\ H_2O$
3. $Er(No_3)_3 \cdot 5\ H_2O$
4. $Ce(No_3)_3 \cdot 6\ H_2O$ 5. Al (No$_3$)$_3$.9 H$_2$O
6. Ni(No$_3$)$_2$.6 H$_2$O
7. Mn(No$_3$).4 H$_2$O
8. Pr(No$_3$)$_3$.6 H$_2$O
9. Y(No$_3$)$_3$.6 H$_2$O
10. Co(No$_3$)$_2$. 6 H$_2$O
11. ZrO(No$_3$)$_2$.x H$_2$O
12. Sm(No$_3$)$_3$.6 H$_2$O
13. Nd(No$_3$)$_3$.6 H$_2$O
14. Eu(No$_3$)$_3$.5 H$_2$O
15. Dy(No$_3$)$_3$.x H$_2$O
16. Yb(No$_3$)$_3$.5 H$_2$O
17. Ti(No$_3$)$_4$.4 H$_2$O
18. Bi(No$_3$)$_3$.5 H$_2$O
19. Au Cl
20. Sr(No$_3$)$_2$
21. Mg(No$_3$)$_2$.6 H$_2$O
22. La(No$_3$)$_3$.6 H$_2$O
23. Ag No$_3$.
24. In(No$_3$)$_3$.X H$_2$O
25. Cd(No$_3$)$_2$.4 H$_2$O
26. V(No$_3$)$_2$
27. Zn(No$_3$)$_2$.6 H$_2$O
28. Dy(No$_3$)$_3$.xH$_2$O
29. Tb(No$_3$)$_3$.5 H$_2$O
30. Ca(No$_3$)$_2$.4H$_2$O
31. C$_4$ H$_4$ NNbo$_9$.x H$_2$O
32. Pb(No$_3$)$_2$
33. Nb(No$_3$)$_3$.5H$_2$O
34. Hf(No$_3$)$_4$
35. Zr (So$_4$)$_2$.H$_2$O
36. Gd(No$_2$)$_3$.6 H$_2$O
37. Sc(No$_3$)$_3$
38. Ga(No$_3$)$_3$.xH$_2$O
39. Cu(No$_3$)$_2$.xH$_2$O
40. V$_2$ O$_5$
41. In(No$_3$)$_3$.xH$_2$O
42. Zr(No$_3$)$_4$
43. Na$_2$ SiO$_3$
44. Na$_2$ O$_3$ Si.9H$_2$O The loading body material then serves as a coloring solvent reservoir and as a reservoir for stabilizer solutions for the full loading of all porosities of the porous ceramic. Color-producing components of the coloring pigment solution and/or stabilizer solutions are understood as any color-producing and non-color-producing components that result in the desired and stress-free sinterable ceramic blanks. Chemical stabilizers are understood as any stabilizers that are capable of influencing the technical parameters of the zirconium oxide.

According to the invention, the desired distribution control step of the color-producing concentrations of organic and inorganic salts takes place in a controllable sealing means and/or isolating means, for example in a mold. The mold can preferably be made of silicone, for example. Surprisingly, it has been discovered that a distribution control step that is similar to the convection of a fluid in a vessel will also take place in a porous ceramic that is located inside a silicone housing. In the process according to the invention, any convection may be used, preferably chemical convection. In one solution, solutal convection may also be used, and in the case of a salt solution, haline convection and thermohaline convection may be used, along with Mahagoni convection and electrical convection. The convection is generated based on the substance properties, the molded body, by the flows that are influenced, by an exchange of energy, entropy, substances and electrical charges, among other things by diffusion, phase transitions, drying, absorption, evaporation, solidification, dissociation, lissociation and friction. In addition, a surface may act as a catalyst. For these reasons, convection is also difficult to calculate. Through many hundreds of experiments performed among thousands of possibilities, the adjustments for a distribution control step that behaves in a precise manner by means of haline convection have been ascertained. Convection based on gravity and density differences is further controlled by the volume of organic and inorganic salts, and by temperature differences, electrostatic fields and the humidity of the surrounding air, and by the formation of open or covered surfaces of the porous ceramic blank. The porous ceramic blank may be round or horseshoe-shaped, and can have a height of 10-50 mm and a diameter of 10-150 mm, or may correspond to the enlarged shape of an entire jaw. To conserve material, the blank may be provided with recesses.

To transport the controllable coloring pigment solution and/or the pure stabilizer solutions, water or a mixture of water with an organic, in particular a polar organic solvent is used according to the invention. As color-producing components, fireproof pigments and/or oxides and/or coloring and fluorescent metal oxides and/or organic or inorganic salts that contain zirconium oxide-stabilizing groups are used, and are dissolved using an aqueous solution or distillate with an alcohol base. Organic solvents are aliphatic alcohols, for example. The solvent and/or transport fluid may optionally contain additives, such as stabilizers or electrolytes, complexing agents, dispersants, etc. The additives are contained either in the loading body material or in the coloring pigment solution and/or the coloring pigment stabilizer solution. A coloring pigment solution and/or coloring pigment stabilizer solution is also understood as any solution that can be located in the porosities of a porous ceramic and can be distributed in a controlled manner through open and closed areas of the porous ceramic blank.

It is further expedient for chemical stabilizers, such as cerium chloride, cerium nitrate or ammonium cerium nitrate, for example, to be introduced into the coloring pigment solution and/or coloring pigment stabilizer solution. Cerium chloride is converted by an oxidizing agent, at a temperature of about 60°-110° in a solution having a pH value of 5-9, to cerium oxide, which is calcined in the pores of the prefabricated zirconium blank, and thereby binds homogeneously to the zirconium oxide lattice. The same is true for yttrium and/or zirconium nitrates and the compounds thereof that are capable of stabilizing the zirconium oxide. Thus the loading and distribution control steps result not only in coloring, but also in the possibility, according to the invention, of introducing into the prefabricated zirconium blank zones of the zirconium oxide ceramic that have different physical properties by using appropriate stabilizers. Appropriate additives and oxidizing agents include aluminum nitrate, sodium hydroxide, potassium hydroxide, hydrogen peroxide, iodide salts, zirconium(IV) oxynitrates, hydronium nitrates, hypochloric acid, sodium hypochlorite, calcium hypochlorite, etc. In this manner, according to the invention, mean particle sizes of about 0.01μ to 0.5μ and a crystal diameter of about 1 nm to 80 nm (e.g. of cerium oxide) can be produced in the pores of the prefabricated porous ceramic in one or more loading steps. It is likewise expedient for oils and/or benzines to be introduced into the coloring pigment solution and/or the coloring pigment stabilizer solution, and for flow-reducing filters to be placed between the loading body reservoir and the silicone housing. The loading body then functions as a flow-reducing filter, and ensures first, that the fewest possible concentration accumulations find their way into the porous ceramic blank, and second, that a capillary suction loading is achieved. Since the bearing surfaces of the porous ceramic always contain zircon dust, the coloring pigment solution and/or the coloring pigment stabilizer solution becomes contaminated, and as a result, the loading body materials and/or the capillary flow reducer act as filters.

In a possible process variant according to the invention, the coloring pigment solution and/or the coloring pigment stabilizer solution and/or the fireproof pigments and/or oxides and/or coloring and fluorescent metal oxides and/or the organic or inorganic salts are loaded into the convection housing in/under a vacuum atmosphere and/or an inert gas atmosphere (argon). The color-producing components and/or the fireproof pigments and/or the oxides and/or the coloring and fluorescent metal oxides and/or the organic or inorganic salts of the coloring pigment solution and/or stabilizer solutions may also be transported under nearly a vacuum atmosphere. However, this is not imperative. Depending on the porosity of the ceramic blank, excessively strong suction can result in unfilled pores, and/or in undesirable concentration accumulations of the color-producing components.

In a further process variant according to the invention, the coloring pigment solution and/or stabilizer solutions and/or the fireproof pigments and/or the oxides and/or the coloring and/or fluorescent metal oxides and/or the organic or inorganic salts are transported under pressure by haline convection. Thus the capillary pressure can also be increased by an application of pressure using a capillary pressure-retaining device for the purpose of loading with solvent from a loading body material. Too much pressure can lead to an overfilling or underfilling of the porosities and the cavities thereof, and can cause severe blockages, which lead to undesirable concentration accumulations of the color-producing components. The capillary pressure-retaining device for loading with solvent from a loading body material is understood as any dense layer or absorbing device in which or on which solutions that contain color-producing and non-color-producing components and/or chemical stabilizer components can be stored, with an increase and/or decrease of the capillary pressure in the porosities of the ceramic.

In the process according to the invention, the coloring pigment solution and/or coloring pigment stabilizer solution with fireproof pigments and/or oxides and/or coloring and fluorescent metal oxides and/or organic or inorganic salts and/or color-producing chemical stabilizers is introduced into the pores of the porous ceramic using a capillary pressure-retaining loading body material by means of capillary suction loading. On the surface of the ceramic are pore openings into which the color-producing components and/or fireproof pigments and/or oxides and/or coloring and fluorescent metal oxides and/or organic or inorganic salts and/or color-producing chemical stabilizers penetrate. The penetration depth is dependent on the volume of coloring pigment solution and/or coloring pigment stabilizer solution, the adjusted capillary pressure and the capillary pressure of the capillary pressure-retaining device for loading with solvent from a loading body material. The capillary pressure of the capillary pressure-retaining device for loading with solvent from a loading body material should be lower than the capillary pressure of the porous ceramic and should load all porosities uniformly with coloring pigment solution and/or coloring pigment stabilizer solution, at a rate that is not too rapid, and without air pockets.

Expediently, the loading body materials are filled with color-producing components and are used as solvent reservoirs, which serve as simple stores for color mixtures or as filters. Drink mats, for example, would then contain the desired concentrations and color-producing components for the tooth color and/or the chemical stabilizers. Capillary pressure-retaining loading bodies further contain the complex solutions (complex solutions are any salts of the rare earth elements group, etc.). The drink mat is placed on the surface of the porous ceramic blank, which is located, e.g. in a silicone housing. The silicone housing, together with the porous ceramic, is then placed flat on the capillary pressure-retaining device, for loading with solvent from a loading body material. In this way, any point in the porous ceramic block can be loaded with the coloring pigment solution and/or the coloring pigment stabilizer solution. Loading is understood as any type of wetting that induces at least an ion covering with ceramic particles in the pressed blank form, utilizing the cavities between the different ceramic particles. Loading body materials are understood as any materials and substances that are permeable to liquid and/or act as flow-reducers and/or are capable of retaining capillary pressure.

The distribution control step is controlled by the silicone housing, the nitrate concentration, the temperature, the air humidity, and by areas of different sizes that are in contact with the surrounding air humidity. Care must be taken to ensure that the surrounding air humidity does not drop below about 30% at temperatures of about 25°. Otherwise, the movement of the coloring pigments and/or the zirconium oxide stabilizers will result in a very substantial concentration accumulation. However, this is dependent on the degree of porosity of the ceramic body in each case.

During the process according to the invention, it is advantageous for color measurements of natural teeth to be stored in a programmable memory, so that the color of the natural teeth can be reproduced using the appropriate coloring pigment solution and/or coloring pigment stabilizer solution. The tooth color of the patient's natural teeth is subsequently measured. The collected color data are then stored in software or in a programmable memory. The software or the programmable memory can use the color data for the natural tooth color to calculate or reproduce the coloring pigment solution and/or coloring pigment stabilizer solution. The color progression is then displayed graphically by the CAD/CAM system. This allows a customer in a dental laboratory to compile the color and physical parameters digitally and place an order based on these.

It has further surprisingly been discovered that, by covering or masking longitudinal, zebra-like strips of the porous ceramic, a spatially extending color concentration wave and/or stabilizer concentration wave can be produced in the ceramic block beneath the zebra-like strips that are not masked. Open or annular maskings will result in a spatial, tapered cone of color concentration and/or in stabilizer concentration waves. If the desired fields are surrounded by frames of different heights, a higher air humidity will develop within the frame, even though the surrounding air humidity remains constant. The areas with the high frame and higher air humidity will form a spatially higher, vertically extending color concentration with or without chemical stabilizers. The areas with the low frame and lower air humidity will form a more color intensive and spatially lower color concentration with or without chemical stabilizers of the zirconium oxide.

As a further possibility of the process according to the invention, a program-controlled machine or a device, in particular a CAD/CAM system, can search through the available concentration zones and select those fields of the ceramic blanks in which the color concentration or stabilizer concentration corresponds to the tooth color and the physical properties of the natural teeth, and then mill those fields. For example, a lower hardness in the critical occlusal region. In addition, the loading body material can be milled out to a desired shape with a desired color progression, see FIG. 8 and FIG. 9, or can have the anatomy of the surface of a dental prosthesis. Surprisingly, it has been discovered that the process according to the invention, which decreases the porosity of the ceramic blank, increases its edge stability at the same time. This is particularly advantageous in connection with 3-D printed ceramic structures, which have very high porosity and thus are very difficult to mill. The quality of milling along thin crown margins, for example, can thus lead to chipping on the edge. The milling times for CAD/CAM systems can therefore be reduced by about 25%, making the costly CAD/CAM systems more cost-effective and efficient, thus contributing to their amortization.

Further according to the invention, the colors of the color measurements that are taken are stored and transmitted to the program-controlled machine or to the program-controlled device. The previously collected color data for the natural teeth of the patient are transmitted to the program-controlled machine or the device, so that the machine uses one or more loading body materials, which it places, e.g. in a silicone housing in order to produce the tooth color and/or the hardness of the patient's natural teeth.

In an advantageous process variant, entire presintered and/or prepressed ceramic blocks are colored prior to CAD/CAM processing. This means that ceramic blocks are produced with the desired density, and already having various basic colors and/or material compositions. It thus remains only to produce the concentration of the stabilizers, e.g. in wave form and/or in spatial conical form, in the desired areas by means of a distribution control step. Increased fissure resistance or a reduced hardness can optionally be adjusted. Advantageous porous ceramics are, e.g. 3Y-TZP, cubic 5Y-TZP and Ce-TZP.

A process for producing a polychromatically and/or spatially polychromatically colored and/or a monochromatically colored, prefabricated ceramic body, in particular a dental ceramic blank of this type, is characterized in that the residual porosities of a prefabricated ceramic blank exhibit a weight increase of about 0.01%-25% after drying, as a result of a loading step and/or a distribution control step with pigment solutions and stabilizers. For one embodiment of the process, a porous fired ceramic white or a porous pressed glass ceramic is used as the ceramic. This process may be used with all porous ceramics. This is independent of whether the ceramic is a pressed, fired, bound, unbound and/or a sintered ceramic. However, the ceramic must have pores in order for the color-producing components and/or the fireproof pigments and/or the oxides and/or the coloring and fluorescent metal oxides and/or the organic or inorganic salts to allow the coloring pigments and/or the stabilizers to move in at least one direction.

A process for producing a polychromatically and/or spatially polychromatically and/or a monochromatically colored prefabricated ceramic body, in particular a dental ceramic blank that is colored in this manner, in which the hardness and/or the fissure resistance is adjusted by means of the loading step and/or the distribution control step, dependent on the chemical stabilizers that are located in the porosities of the prefabricated ceramic blank. In the process, for example, a porous ceramic composed of lanthanum oxide ($La_2O_3$), silicon dioxide ($SiO_2$), leucite, vanadium(V) oxide ($V_2O_5$), cerium oxide, erbium oxide, zirconium oxide (ZrO2), yttrium oxide (Y2O3), hafnium oxide (HfO7), aluminum oxide (Al2O3), phosphorus oxide ($P_2O_3$, $P_2O_4$, $P_4O_{10}$), titanium oxide ($TiO_2$), tin oxide (SnO, $Sn_2O_3$, $SnO_2$), boron oxide (($BO)_x$, $(B_2O)_x$), boron trioxide ($B_2O_3$), fluorine ($F_2$), sodium oxide ($Na_2O$), barium oxide (BaO), strontium oxide (SrO), strontium peroxide ($SrO_2$), magnesium oxide (MgO), zinc oxide (ZnO), tin oxide (SnO, $Sn_2O_3$, $SnO_2$), calcium oxide (CaO), titanium oxide ($TiO_2$), niobium oxide (NbO, $NbO_2$, $Nb_2O_5$), tantalum oxide (TaO, $TaO_2$, $Ta_2O_5$), doped spinels and/or other oxides and mixtures thereof is used.

A process for producing a polychromatically and/or spatially polychromatically and/or a monochromatically colored prefabricated ceramic body, in particular a dental ceramic blank that is colored in this manner, characterized in that once the coloring pigment solution and the stabilizers in the porosities are dried, an oxidation phase of the doping is carried out at approximately 100° to 800° and/or a calcining phase is carried out at approximately 800° to 1500°, for approximately 1 to 24 hours. In addition, feldspar ceramic, zirconium oxide-reinforced and/or leucite-reinforced ceramic, lithium silicate glasses or lithium silicate glass ceramic or lithium disilicate glass ceramic, silicate ceramic and/or oxide ceramic may be colored using the process according to the invention. For the process, any oxide ceramic or any ceramic that is based on an oxide ceramic may be used as the ceramic to be colored. Oxide ceramics are high-performance ceramics that are harder, more wear-resistant, more heat resistant and more brittle than hard metals. They therefore possess the properties that are most important for a prosthetic implant or an implant and/or for a dental prosthesis. A ceramic that is based on glass ceramic and/or glass may also be used.

A process for producing a polychromatically and/or spatially polychromatically and/or a monochromatically colored prefabricated ceramic body, in particular a dental ceramic blank that is colored in this manner, is characterized in that, during the loading step and the distribution control step, coloring pigments and stabilizers are introduced into a commercially available 3Y-TZP body in order to produce a CE-TZP from a 3Y-TZP. In a process according to the invention, the color-producing component is sintered in the porous ceramic blanks under an increasing vacuum atmosphere or in an oxygen-free or virtually oxygen-free space, in order to oxidize, calcine and fix the color-producing components and/or the fireproof pigments and/or the oxides and/or the coloring and fluorescent metal oxides and/or the organic or inorganic salts in the ceramic. This means that the color-producing components and/or the fireproof pigments and/or the oxides and/or the coloring and fluorescent metal oxides and/or the organic or inorganic salts are oxidized, calcined and fixed in the pores of the ceramic by a sintering process or directly in a final sintering process, and/or are converted to oxides. A spatially polychromatic ceramic body is also understood as a spatial progression of the transparency that is achieved, for example by the individual crystals of a polycrystalline body, and that is stabilized, for example by the cubic crystals of the zirconium oxide or by yttrium oxide (Y-KZP or with calcium oxide) (CSZ). This is due to the fact that the cubic crystals have no optical anisotropy and thus generate particularly high transparency. In the process according to the invention, these may be colored homogeneously and/or with color concentrated in the pores of the ceramic blank in one or more color tone concentration progressions by means of the distribution control step, depending on the composition of the ceramic blank. For instance, at wavelengths of 600 nm, and with a sample thickness of x=30 mm to x=1 mm, inline transmissions and of 35% T at a wavelength of 600 nm to 95% T at wavelengths of 600 mn may be established. For dental applications, the light refraction index is preferably between 1.20 and 2.20 and particularly preferably between 1.60 and 1.65. Translucency adjustments are made using at least one element, e.g.

$Er(No_3)_3.5\ H_2O$
$Ce(No_3)_3.6\ H_2O$
$Al\ (No_3)_3.9\ H_2O$
$Y(No_3)_3.6\ H_2O$
$Nd(No_3)_3.6\ H_2O$
$Sr(No_3)_2$
$Mg(No_3)_2.6\ H_2O$
$La(No_3)_3.6\ H_2O$
$Zn(No_3)_2.6\ H_2O$
$Ca(No_3)_2.xH_2O$
$Ga(No_3)_3.xH_2O$
$Cu(No_3)_2.xH_2O$
$Zr(No_3)_4$
$Na_2\ SiO_3$
$Na_2\ O_3\ Si.9H_2O$, in an amount of 0.001% to 15% by weight with respect to the ceramic, depending on the composition of the blank. Chromaticity is specified using the L*a*b* system, and may contain a color of each point to another point. This is dependent on the composition and coloring of the ceramic blank. In the case of a dental material, the value L* ranges from 40 to 90, a* ranges from 35 to −35, and b* ranges from −15 to 40. For example, for a finalized sintered ceramic measuring 1.5 mm thick and having a white reference background, values of L*=94, a*=3.87 and b*=−12.85 result.

A process for producing a polychromatically and/or spatially polychromatically and/or a monochromatically colored prefabricated ceramic blank having advantageous physical parameters is characterized by a stabilizer fraction of 0.001 to 50% by weight, preferably of 1.5 to 50% by weight, with respect to the ceramic weight. Each of the stabilizers is loaded relative to the zirconium oxide concentration into the porosities of the ceramic body, and/or during the distribution control step is homogeneously concentrated and/or distributed to desired zones. Suitable for producing advantageous porous ceramics are, e.g. the following: Y-KZP, CSZ, TZP, 3Y-TZP, 5Y-TZP, TZP, SSZ, PSZ, ATZ, CETZP, KSZ, ZrSio4, ZrSi2, and mixtures of the respective powders. For example, a zirconium nitrate can be used for producing pure zirconium(IV) oxide layers. (Reaction of zirconium oxide with silicon: $3Si+Zro_2 \rightarrow Zr\ Si_{2+}Si\ o_2-Zr\ Si_2$). A compound can likewise be produced by fusing $SiO_2$ with $ZrO_2$ using a zirconium salt with a reaction of sodium silicate in an aqueous solution to ($Zr\ SiO_4$). Thus the production process according to the invention also implements the use of all possible advantageous zirconium compounds. The process according to the invention comprises the following steps:

(1) a preparing the ceramic
(2) b sealing and/or isolating the ceramic body by means of a mold
(3) c loading the porosities of the ceramic body, wherein steps (2) b and (3) c may be executed in any sequence
(4) d distribution control step of the color-producing and/or oxidizing stabilizer elements
(5) e removing liquid until the distribution control in the sealed and/or isolated ceramic body is completed
(6) f drying the ceramic blank and/or final sintering or presintering and/or for oxidation phase formation for fixing the salts and oxidation for calcining and/or for final sintering
(7) g CAD/CAM processing
(8) h final sintering and/or sintering for fixing the oxides in a sintering program.

A process for producing a polychromatically and/or spatially polychromatically and/or a monochromatically colored prefabricated ceramic body, in particular a dental ceramic blank that is colored in this manner, with advantageous adjustable technical parameters, is characterized by the fact that only stabilizing solutions are introduced into the pores of the prefabricated ceramic body by means of the loading step and/or the distribution step. The following are contained in the coloring pigment solution and/or the chemical stabilizer solution according to the invention: concentrations of the color-producing components and/or the fireproof pigments and/or the oxides and/or the coloring and fluorescent metal oxides and/or the organic or inorganic salts, along with the zirconium stabilizers that result during the subsequent oxidation and/or the sintering process, and the oxides having a percentage by weight of between 0.001% by weight and 50% to 90% by weight, or between 0.0001% by weight and 10% by weight, with respect to the weight of the ceramic. Either small volumes or larger volumes of color-producing components and/or stabilizing components and/or fireproof pigments and/or oxides and/or coloring and fluorescent metal oxides and/or organic and/or inorganic salts will be required, depending upon the hue that is to be achieved and depending upon which physical parameters are to be adjusted. The concentrations of the color-producing components and the chemical stabilizers and/or the fireproof pigments and/or the oxides and/or the coloring and fluorescent metal oxides and/or the organic or inorganic salts are therefore also contained in the loading body materials, in order to produce and store the desired color and/or the physical parameters.

According to the invention, the coloring pigment solution and/or the dissolved chemical stabilizers and/or the loading body solvent reservoir and/or the loading body materials contain concentrations of all color-producing and non-color-producing components, along with the chemical stabilizers in the solution of zirconium oxide, which can be moved by means of the distribution control step.

The color-producing solution is stably dissolved during the distribution control step, in order to prevent individual elements and/or chemical stabilizer solutions from decomposing and/or settling out of mixed elements of the coloring pigment solution in a direction of movement, in the porosity of the prefabricated blank. Particularly suitable for this purpose are preliminary solutions of, e.g.:

$Zro(No_3)_2.x\ H_2O$
$Ce(No_3)_3.6\ H_2O$
$Al(No_3)_3.9\ H_2O$
$Zr(No_3)_4$
$Y(No_3)_3.6\ H_2O$
$Sm(No_3)_3.6\ H_2O$
$Ca(No_3)_2.xH_2O$
$Gd(No_2)_3.6\ H_2O$ and/or other salts.

According to the invention, all known color-producing components and/or the chemical stabilizers in solution for adjusting the physical parameters of the zirconium oxide ceramic contain organic and inorganic salts that can be used and that convert during final sintering to an oxide. These constituents can function as a color additive or stabilizer and also as a sintering aid. The soluble constituents can be incorporated into the crystal lattice and substituted, or can be precipitated in the form of compounds, e.g. mixed crystals, in the grain boundary phase, and can form entirely new parts of stabilized zirconium crystals or mixed crystals in the porosities of the prefabricated ceramic body blank. The environment also influences the formation of crystals. As this has not yet been researched, additional, as yet unknown physical properties will be discovered in the future. Thus far, science also has found no explanation for the phase transition behavior of the zirconium as a result of the stabilizers. The important physical properties, those of Y3-TZP, Y5-cubic TZP, and Ce-TZP, can thus each have a Vickers hardness, Hv10 of between 400 and 1650 and a fissure resistance, MPa of between 4.5 and 16.5, and can be adjusted spatially polychromatically, dependent on the loading of the porous ceramic blank and the desired use thereof (framework or monolithic dental prosthesis). Thus the listed ceramics can be, with at least one element, e.g.:

$Zro(No_3)_2.x\ H_2O$
$Ce(No_3)_3.6\ H_2O$
$Al\ (No_3)_3.9\ H_2O$
$Y(No_3)_3.6\ H_2O$
$Sm(No_3)_3.6\ H_2O$
$Ti(No_3)_4.4\ H_2O$
$Sr(No_3)_2$
$La(No_3)_3.6\ H_2O$
$V(No_3)$
$Zn(No_3)_2.6\ H_2O$
$Ca(No_3)_2.xH_2O$
$Hf(No_3)_4$
$Zr\ (So_4)_2.H_2O$
$Gd(No_2)_3.6\ H_2O$
$Sc(No_3)$

In one or more loading steps, the physical properties can be established in desired zones of the ceramic blank. This is dependent upon which physical parameters are to be adjusted. The stabilizer solutions have concentrations of 0.001% to 30% by weight, with respect to the weight of the ceramic blank. The physical values, e.g. of a 70% zirconium oxide ceramic are listed in the table, along with examples of values.

A further embodiment example according to the invention is a loading body, which may have any form, with the color-producing components and/or non-color-producing components, introduced by means of solvent into the loading body material, and/or the fireproof pigments and/or the oxides and/or the coloring and fluorescent metal oxides and/or the organic or inorganic salts containing at least one of the elements yttrium, iron, titanium, selenium, silver, indium, gold, chromium, copper, praseodymium, cobalt, nickel, manganese, erbium, neodymium, cerium, aluminum, zirconium or rare earth metals, or mixtures thereof. The loading bodies can also be stored under capillary pressure with the coloring pigment solution and/or the coloring pigment stabilizer solution in an air tight package.

Additionally, the layer thickness of the loading bodies that are used in and/or on the capillary pressure-retaining device for the purpose of loading with solvent from a loading body material, for the purpose of reducing capillary force, and as filters is between 0.01 mm and 250 mm. The layer thickness varies within the aforementioned range and is dependent on the diameter of the ceramic body, on the porosity, and on the concentration of the coloring pigment solution and/or the coloring pigment stabilizer solution. The coloring pigment solution and/or the coloring pigment stabilizer solution can also be dried in the loading bodies, so that capillary pressure can then be built up again on the solvent reservoir from the loading body material and/or from the capillary pressure-retaining device for the purpose of loading with solvent from a loading body material, thereby loading the porosities with the coloring pigment solution and/or the coloring pigment stabilizer solution and the solution of chemical stabilizers.

It is likewise expedient for the coloring pigment solution and/or the coloring pigment stabilizer solution with the fillers contained therein and the color-producing components and/or the fireproof pigments and/or the oxides and/or the coloring and fluorescent metal oxides and/or the organic or inorganic salts of the chemical stabilizers for zirconium oxide to be stored in the loading body material. The loading body materials have various adaptable geometric shapes. This also means that the coloring pigment solution and/or the coloring pigment stabilizer solution in the loading body materials are under the same capillary pressure. The loading body materials can now be adapted side by side, one on top of the other or one in front of the other on the ceramic blanks, without the coloring pigment solution and/or the coloring pigment stabilizer solution becoming intermixed. The size or volume and the material selection of the loading body materials allows a desirable volume of color-producing components and stabilizers to be stored.

DESCRIPTION OF THE SEVERAL VIEWS OF THE DRAWINGS

Not all materials and/or components or color-producing components/substances that can be used in the process according to the invention are listed. However, all options should be known to a person skilled in the art from the above specifications. Additional details, features, combinations of features and effects that are based on the invention will be apparent from the following description of preferred exemplary embodiments of the invention, and from the set of drawings. Shown in the drawings are.

DETAILED DESCRIPTION

Figure 1:
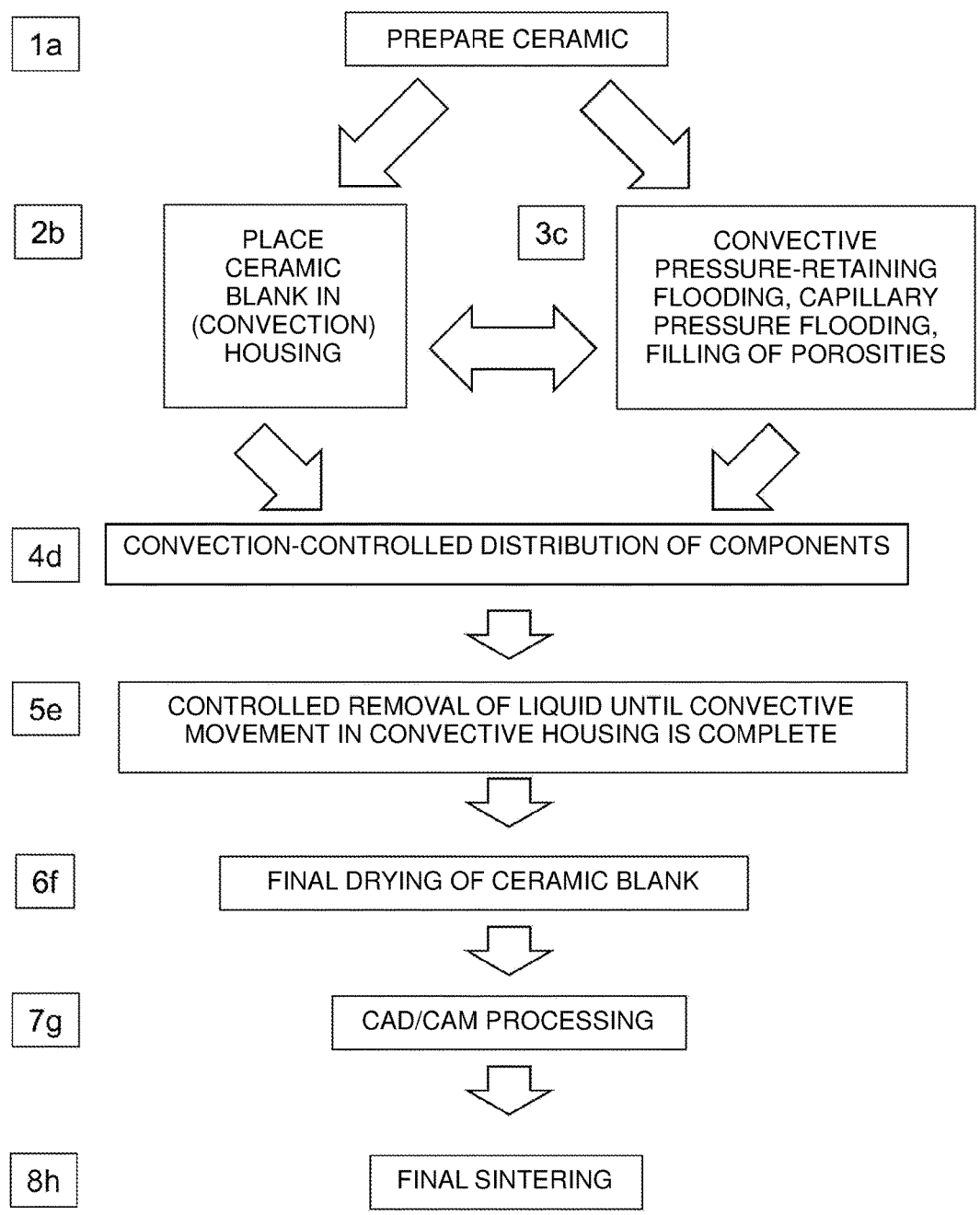
FIG. 1 a flow chart illustrating the process of the invention.

FIG. 1 provides a flow chart of the process according to the invention.

A) Only porous and/or presintered and/or unbound and/or bound ceramics are prepared for CAD/CAM processing.

B) The ceramic body is then placed in a mold that provides the maximum possible air-tightness, sealing and isolation, e.g. in a silicone housing. The size and the parameters of the silicone housing can be freely selected, and the mold may not have any atmospheric pressure or develop such pressure.

C) The coloring pigment solution and/or the coloring pigment stabilizer solution and/or the chemical stabilizers are then introduced into the porosities of the porous ceramic blank by airless loading by means of the capillary pressure-retaining device for loading with solvent from a loading body material. Suitable for this purpose are all loading body materials of the capillary pressure-retaining device for loading with solvent from a loading body material, which device may also be equipped with a capillary pressure-controlled equalization tank for keeping the capillary pressure constant.

D) At this point, the distribution control step of the color-producing components and/or the coloring pigment solution and/or the coloring pigment stabilizer solution and/or the chemical stabilizers in the porous ceramic begins in the silicone housing. The silicone housing also has open and closed areas, which are surrounded by a certain air humidity in order to control the direction of movement of the coloring pigments and/or the coloring pigment solution and/or the coloring pigment stabilizer solution and/or the chemical stabilizers so as to achieve desired colorings and/or hardness degrees and/or fissure resistance in the oxide ceramic.

E) Liquid is removed until the distribution control step is completed.

F) The porous ceramic is dried for the formation of crystals and/or is subjected to heat treatment for oxide phase formation and/or to calcining and/or to final sintering G) CAD/CAM processing, factoring in any shrinkage compensation H) Final sintering, fixation and conversion of the stabilizers and color-producing components to oxides for stabilizing and calcining, and final sintering in a sintering program.

The silicone housing is sealed as tightly as possible, at least on the side surfaces of the millable ceramic blank, so that a convection flow can be established, as in a vessel. Color-producing and non-color-producing components that have been introduced into the stabilizers and the coloring solution can then be distributed uniformly or in the desired concentration progression. Without sealing and/or isolation by means of a mold, however, this cannot be accomplished in a controlled manner. Congested areas or uncolored areas, as are taught in EP 235 97 71, will result. By enlarging or reducing the open areas of the silicone housing, and under the influence of temperature and the influence of the surrounding, different air humidity, multi-colored spatial color concentration waves or spatial tapered color concentration cones can be established in the ceramic body, along with the technically critical distribution of the chemical stabilizers for adjusting the hardness, allowing the ceramic body to then simulate the natural tooth. For example, EP 29 19 771 and/or Noritake teach layering a ceramic block from dark to light and milling crowns with extensive cutting edges out of the light adjustment zones. In practice, however, there are crowns with extensive cutting edges and an intense color core that cannot be milled from a block that is layered only from dark to light, because no dentine color is layered in the zone with extensive cutting edges. Wolz teaches any angle of the vertical and horizontal tooth axis that can be adjusted and displaced, and that the concentration of a spatial color concentration wave or a spatial tapered color concentration cone can be rotated 360°. Thus it is now possible for the first time to program a plurality of aesthetic options and color zones that have a spatial color progression and adjusted physical parameters by the addition of chemical stabilizers. After drying, crystals form, e.g. in the doped zirconium oxide. The crystals calcine under the influence of temperature to form an oxide phase. The doped stabilizer oxidations are thus very uniformly distributed in the Zr lattice, which is critical for an effective physical final sintering.

The loading body materials may have different concentrations side by side, or may be controlled in sequence. Using the capillary pressure-retaining device for loading with solvent from a loading body material, these materials are placed in the desired positions of the porosity of the ceramic blank and can completely cover the porosities. It has been found that, at a constant capillary pressure, the coloring pigment solution and/or the coloring pigment stabilizer solution and/or the chemical stabilizers can be held one in front of the other or side by side, without intermixing. Thus a multicolored condition can also be achieved, which can now be adjusted for the first time as desired by way of an adjustable step for controlling the distribution of the coloring pigments, including the distribution of the chemically dissolved stabilizers of the zirconium oxide ceramic, e.g. in a silicone housing.

According to the invention, a loading body material for storing solvent, which is filled with porous and/or sponge-like materials, such as microfibers, sponges, cellulose, etc., is located on or below the silicone housing. The loading body material for storing solvent should be capable of absorbing twice as much coloring pigment solution and/or coloring pigment stabilizer solution as the prepared porous ceramic. The loading body materials also store color-producing and non-color-producing components such as chemical stabilizers in solution, which lead to a stress equalization of very high color concentrations in only one region of the ceramic blank during final sintering, which are then compensated for on the opposite side and/or can reduce the hardness of the zirconium oxide ceramic, as is shown, e.g. in FIG. 5. In addition, the production of a partial and/or total prosthetic blank that has a tooth color, a tooth arch, and a pink-colored portion can be adjusted in the silicone housing by means of the distribution control step, until the desired coloring is achieved; see FIG. 10. Loading can be carried out, e.g. using a pure stabilizer solution, in order to selectively move concentrations to desired physical zones of the ceramic blank by means of the distribution control step.

Figure 2:
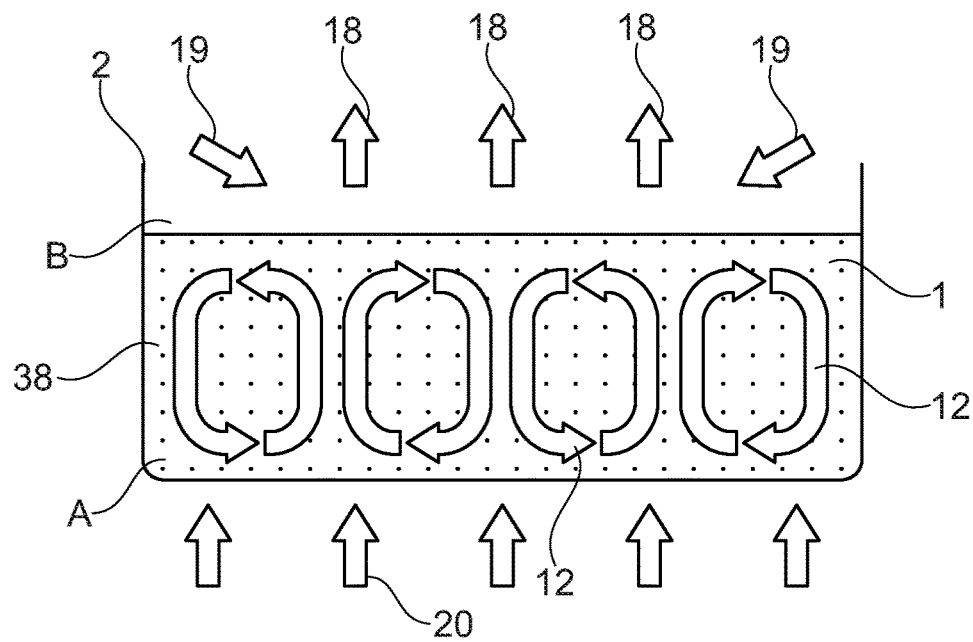
FIG. 2 a cross-section of a monochromatic ceramic blank in the silicone housing, FIG. 3 a cross-section of a polychromatic ceramic blank in the silicone housing, FIG. 4 a cross-section of a polychromatic ceramic blank and of a three-dimensional tapered cone with chemical stabilizers in the silicone housing, FIG. 5 a cross-section of a polychromatic and spatial color concentration wave and of a spatial tapered color concentration cone, with or without chemical stabilizers of the zirconium oxide for programmable CAD/CAM processing, FIG. 6 a concentration equalization in a silicone housing with a loading body, FIG. 7 a silicone housing for equalizing the concentration of the color concentrations, with or without chemical stabilizers of the zirconium oxide and with at least one loading body for storing solvent, in cross-section, FIG. 8 a cross-section of a loading body, FIG. 9 a cross-section of a plurality of stacked loading bodies, FIG. 10 a cross-section of a prosthetic body in a block, FIG. 11 a cross-section of a complete system with the silicone housing and a capillary pressure-retaining device for loading with solvent from a loading body material, with or without chemical stabilizers of the zirconium oxide, FIG. 12 a cross-section of a porous, ceramic body, a distribution control device, and a loading body.

FIG. 2 shows the cross-section of a monochromatic, porous ceramic blank that has been loaded with solvent from a loading body material using the capillary pressure-retaining device for loading. In the silicone housing, liquid is removed. During the distribution control step, the porous ceramic blank is surrounded by the desired concentration in the silicone housing. Without the silicone housing, the porous ceramic blank acts as a ceramic filter, in which undesirable concentrations will collect during infiltration, as is taught by the teaching of DE 10 2008 026 980. Surprisingly, in a silicone housing, the coloring pigment solution and/or the coloring pigment stabilizer solution and/or the chemical stabilizers can be moved in a controlled manner out of these concentration accumulations within the porous ceramic blank. The following procedure may be used to produce uniformly distributed stabilizers and/or chromates in ceramic blanks: both spatially polychromatic or monochromatic colorings and stabilizer complexes can be loaded into prefabricated ceramic blanks using the specified, complex loading medium solutions. The various colors and chromates are known to a person skilled in the art and are described in the cited documents. A preliminary solution of distillate (water) and 0.05% to 50% by weight relative to the concentration of solids of the ceramic, aluminum nitrate or yttrium nitrate or zirconium nitrate or cerium nitrate or polyacrylic salt is used for dissolving the chemical stabilizers. This is mixed on the roller track at about 20 revolutions per minute for 24 hours. The porosity volume of the prefabricated ceramic blank is then determined. With the DD biozirconia that was used, from Dental Direct, ZX 2, diameter 98 mm, height 14 mm, 3Y-TzP, batch No. 50143002, weight 330 gr., a porosity loading volume of 50 g loading solvent was possible. This must be newly determined for each manufacturer. Once this determination has been made, different pigments of the color-producing salts may be added. For example, 1-6 g erbium and 0.1 to 1 g FE are added to 50 g pre-dissolved loading medium solution, and mixed for 1-24 hours on the rolling track. Color adjustments are dependent on the porosity and the purity of the parent materials and on the desired concentration progression of the chromates. The technical requirements must be adjusted. These are described in the disclosed documents. Any mixture of pigment salts and stabilizers may also be fully loaded with color solution into the described loading body material, e.g. drink mat or foam mold, or dried after loading. Alternatively, a loading control step may also be carried out using only stabilizer mixture. The color-producing components are supplied to the ceramic on surface A of the porous, ceramic blank, by means of the capillary pressure-retaining device for loading with solvent from a loading body material, by capillary suction loading, and the ceramic is then rotated 180°, as long as the silicone housing has no coverings that may be displaced (see FIG. 2). All color components 4 then migrate to the surface B of the porous ceramic blank. Once about 80% to 90% of the liquid has been removed, which takes place at less than 70% air humidity on surface B, the blank is then rotated 180° again, as long as the convection housing has no coverings that may be displaced. In this way, a homogeneous distribution of the concentration is accomplished, since the liquid is removed before color concentrations and/or coloring pigment stabilizer solution and/or concentration accumulations of chemical stabilizers can again form from the solution of chemical stabilizers. The specifications are dependent on the adjusted viscosity of the coloring pigment solution and/or the coloring pigment stabilizer solution and the porosity of the ceramic blank.

Figure 3:
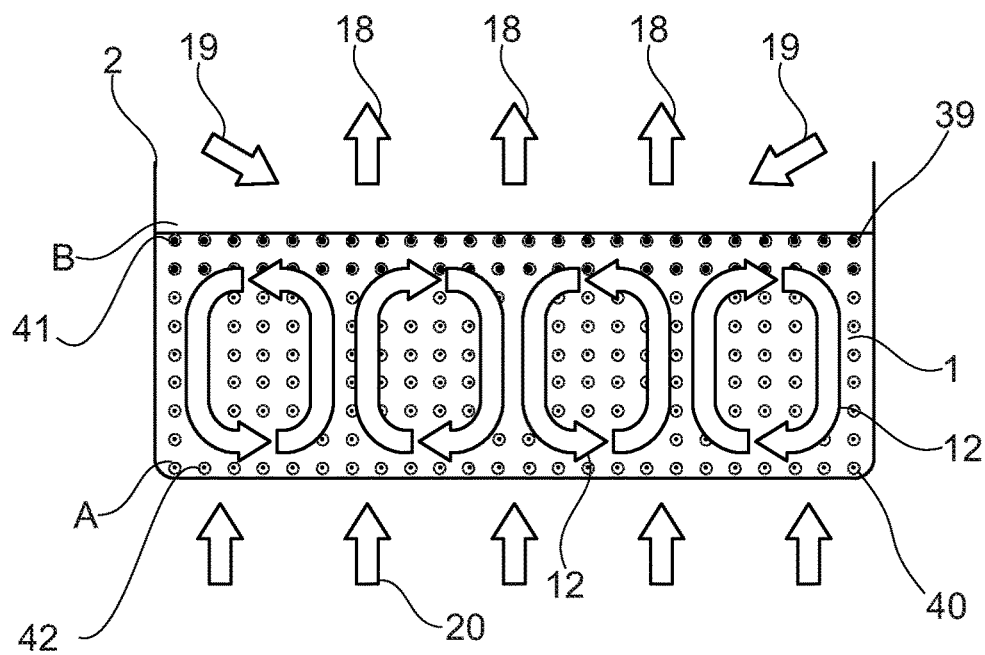

FIG. 3 shows a cross-section of a polychromatic, porous ceramic blank, in which a color-producing concentration progression and stabilizers from dark to light is produced. Surface B is loaded with solvent from a loading body material, using the capillary pressure-retaining device for loading, after which liquid is removed in the silicone mold. The color-producing components can be introduced one after the other, one on top of the other, or one in front of the other, under capillary pressure, into the loading body material, depending on the desired color or the technically desired physical parameters. A simple capillary suction loading with a color component solution naturally also generates a distribution controlled color progression from dark to light on surface B, which is in contact with an air humidity of 30% to 80%. It has been discovered that, e.g. 50% air humidity generates greater movement of the coloring pigments and/or the chemical, dissolved stabilizers, resulting in a stronger progression, i.e. from darker to lighter. At 80% air humidity, a more gentle progression results, i.e. from less dark to less light. Thus zones that have dark concentration accumulations also contain greater stabilizer concentrations. The stabilizer concentrations thus can also be made visible by the coloring pigments. Liquids are removed from the porous ceramic blank until the components can no longer be moved. The drying time is dependent on the porosity and the size of the porous ceramic blank and on the air humidity, the room temperature and the desired concentrations of the components.

Figure 4:
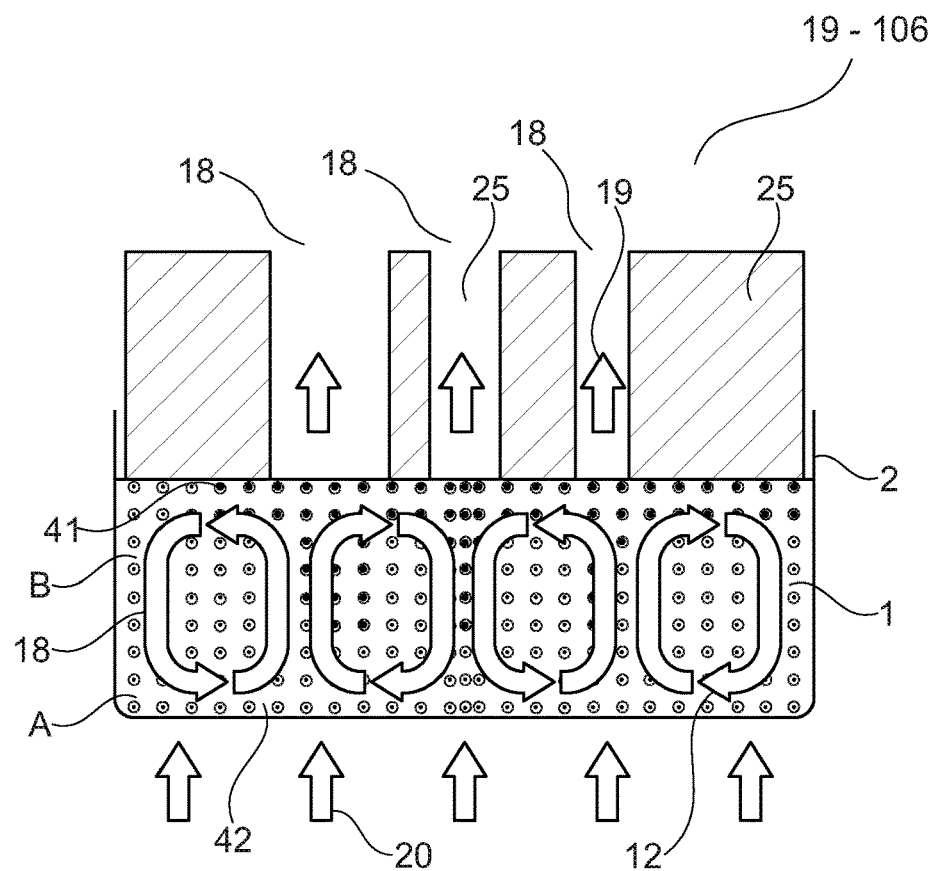

FIG. 4 shows the cross-section of a polychromatic ceramic blank, which also has three-dimensional color zones. Surface B is pressed by means of a capillary pressure-retaining device for loading with solvent from a loading body material into a convection housing that has corresponding surfaces and/or frames that are as air-tight as possible, and liquid is then removed. To support the capillary pressure-retaining device for loading with solvent from a loading body material, loading body materials may also be supplementary materials for loading body solvent reservoirs (as in FIG. 8 and FIG. 9). Surprisingly, the visible movement flow is strong enough that the porous ceramic blank can also be loaded with a color-producing solution and/or a stabilizing component solution by means of a simple, capillary pressure-retaining device for loading with solvent from a loading body material, and after loading, the ceramic blank can be masked, e.g. with strips of adhesive tape, in order to generate open or covered areas. The distribution control step can be intense enough to cause the color-producing components to migrate from all the regions that are filled with them to the open areas.

Figure 5:
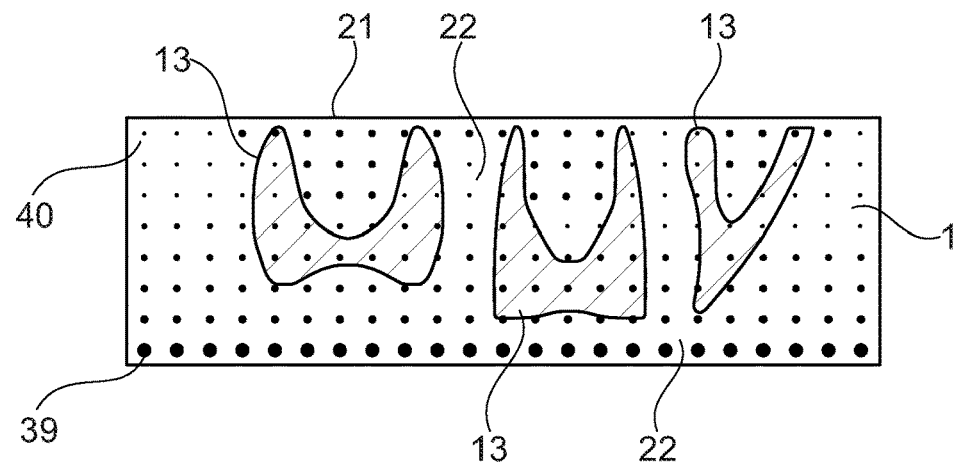

FIG. 5 shows a cross-section of a porous ceramic blank, which also has three-dimensional physical zones and is dried. The physical color progression of the zones is displayed graphically using software (13). The dental technician may select the desired tooth color concentration progression and the concentration progression (21) (22) (39) (40) himself or may base this selection on digital physical data. The CAD/CAM system then mills the dental prosthesis (13) out of the corresponding zones of the ceramic blank (1).

Figure 6:
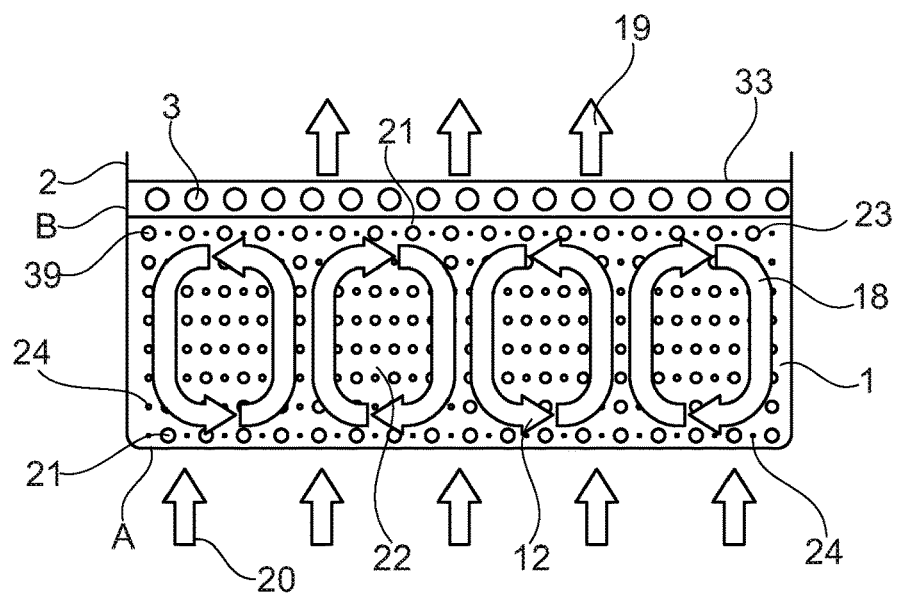

FIG. 6 shows a cross-section of a porous ceramic blank that is already dried and has a strong color concentration component (21) in surface area A. During final sintering, depending on the porosity and the process used to produce the ceramic blanks (1), stresses can develop in the finalized sintered ceramic blank. These stresses can be compensated for by the process used to produce the porous ceramic blank. For this purpose, a loading body material with the corresponding, non-color-producing components and/or the chemical stabilizers for adjusting desired physical properties is simply added to the already dried, porous ceramic blank by means of capillary suction loading, as shown in FIG. 6. The concentration is calculated and is then equalized with non-color-producing components, such as yttrium nitrate, aluminum nitrate, cerium nitrate, zirconium nitrate, potassium nitrate, calcium nitrate, zinc nitrate and lanthanum nitrate. This is done in order to simultaneously reduce the hardness in the occlusal region (chewing surface in the tooth region), for example. However, this can also be accomplished by calculating the loading body materials that are introduced one in front of the other or one on top of the other under capillary pressure into the porous ceramic by means of the capillary pressure-retaining device for loading with solvent from a loading body material.

Figure 7:
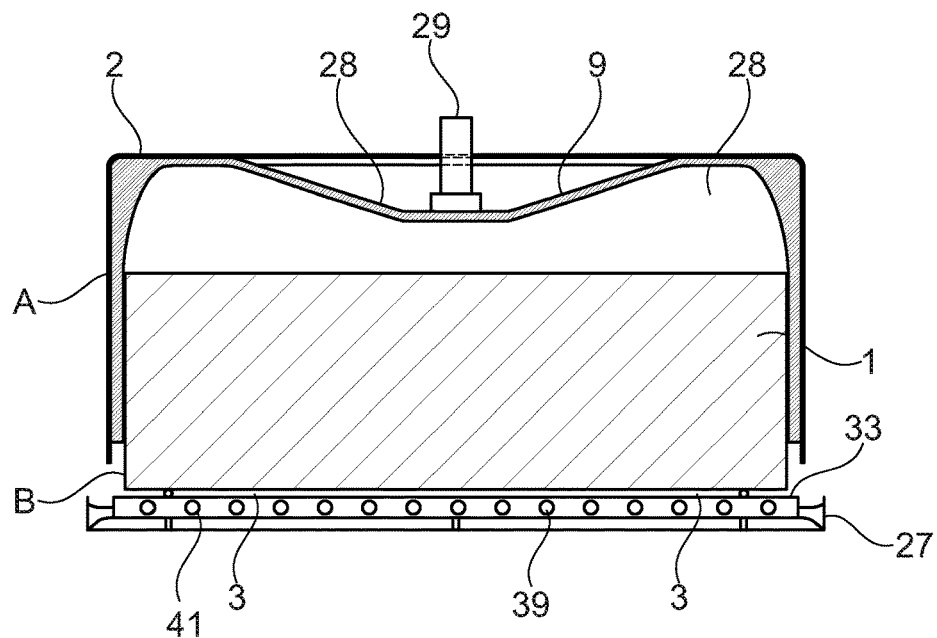

FIG. 7 shows a cross-section of the capillary pressure-retaining device for loading with solvent from a loading body material in a silicone mold housing. The porous ceramic blank is pressed into the silicone mold housing, and the atmospheric pressure is decreased using a valve or a plunger. The porous ceramic blank is placed with surface B on the dry loading body material, which is a loading body solvent reservoir and which is particularly under capillary pressure, and capillary suction loading is generated. The capillary spaces of a ceramic blank that measures 14 mm in height and has a diameter of 98 mm require about 50 g of coloring pigment solution and/or coloring pigment stabilizer solution and/or chemical stabilizers for filling the capillary spaces, which is achieved by capillary suction loading in the silicone housing in about 25 min. However, the time is dependent on the concentration of the coloring pigment solution and/or the coloring pigment stabilizer solution and/or the chemical stabilizers, the adjusted viscosity, the capillary pressure support provided by circumstances in the silicone housing and the nature of the material or the size of the porosities.

Figure 8:
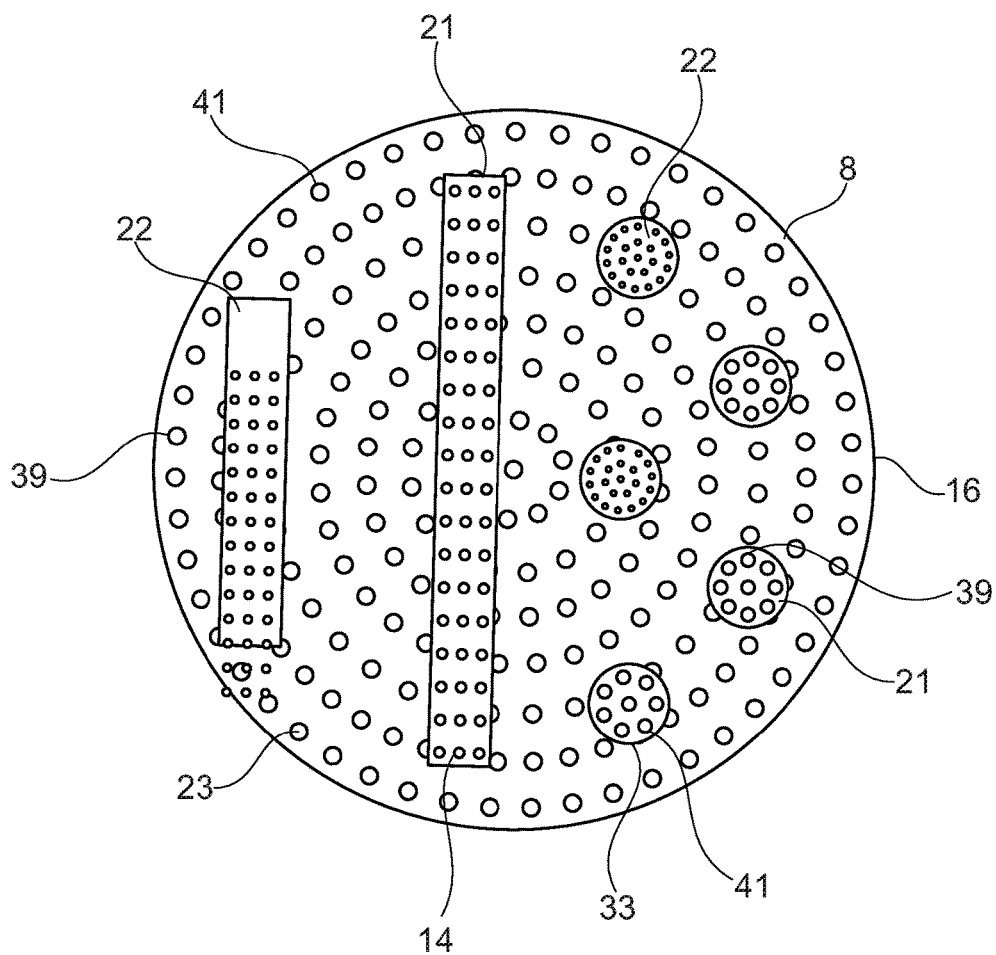
Figure 8:
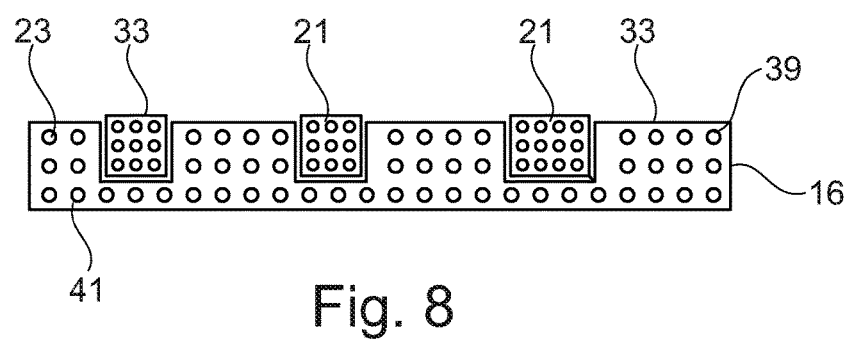

FIG. 8 shows a cross-section of loading body materials that produce color-producing or non-color-producing components and stabilizer components in the porous ceramic by means of capillary suction loading. In this case, the loading body materials are under the same capillary pressure. Thus the various color components and/or the non-color-producing components and/or the solutions of the chemical stabilizers do not intermix. In this way, any possible colorations and stress equalizations along with physical properties can be established in the porous ceramic side by side, or one in front of the other, or one on top of the other by means of loading with coloring pigment solution and/or with coloring pigment stabilizer solution. It is also very important that any coloration contours, such as a jaw shape, individual tooth shapes, implant shapes or abutment shapes, in the horizontal or vertical cross-section can be produced from the loading body materials by cutting out, milling, punching or plotting, etc. The capillary volume of the loading body materials relative to the capillary volume of the porous ceramic can be calculated for the purpose of adjusting the concentration progression.

Figure 9:
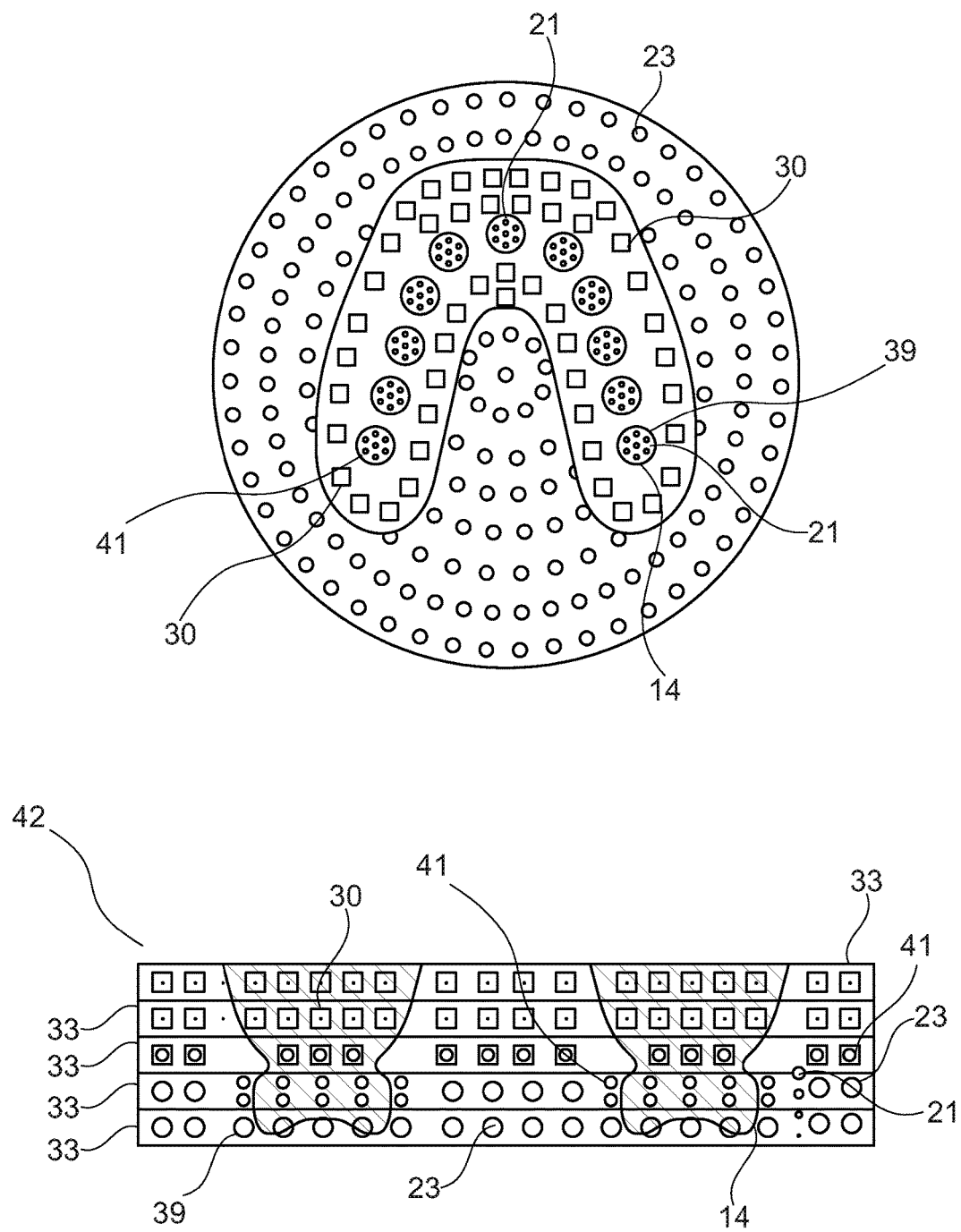

FIG. 9 shows the cross-section of five layered loading body materials for producing three-dimensional prosthetic bodies. For example, five loading body materials are placed one on top of the other. Drink mats measuring 1.4 mm in thickness and having a diameter of 104 mm are suitable for this purpose. These can easily store more than 10 g of coloring pigment solution and/or coloring pigment stabilizer solution and/or color-producing components and/or solutions of the chemical stabilizers for the zirconium oxide. This means that the required coloring pigment solution and/or coloring pigment stabilizer solution and/or the solutions of the chemical stabilizers are stored in the volumes of the five loading body materials, without intermixing, and are introduced into the porous ceramic blanks under capillary suction loading by means of the capillary pressure-retaining device for loading with solvent from a loading body material. The liquid is then removed in the silicone housing. The liquid removal rate is then 24 hours per 1.0 mm of porous ceramic, depending on the composition of the coloring pigment solution and/or the coloring pigment stabilizer solution and/or the solutions of the chemical stabilizers and how these were produced and/or depending on the adjustment of the ambient air humidity between 50% and 90%.

Figure 10:
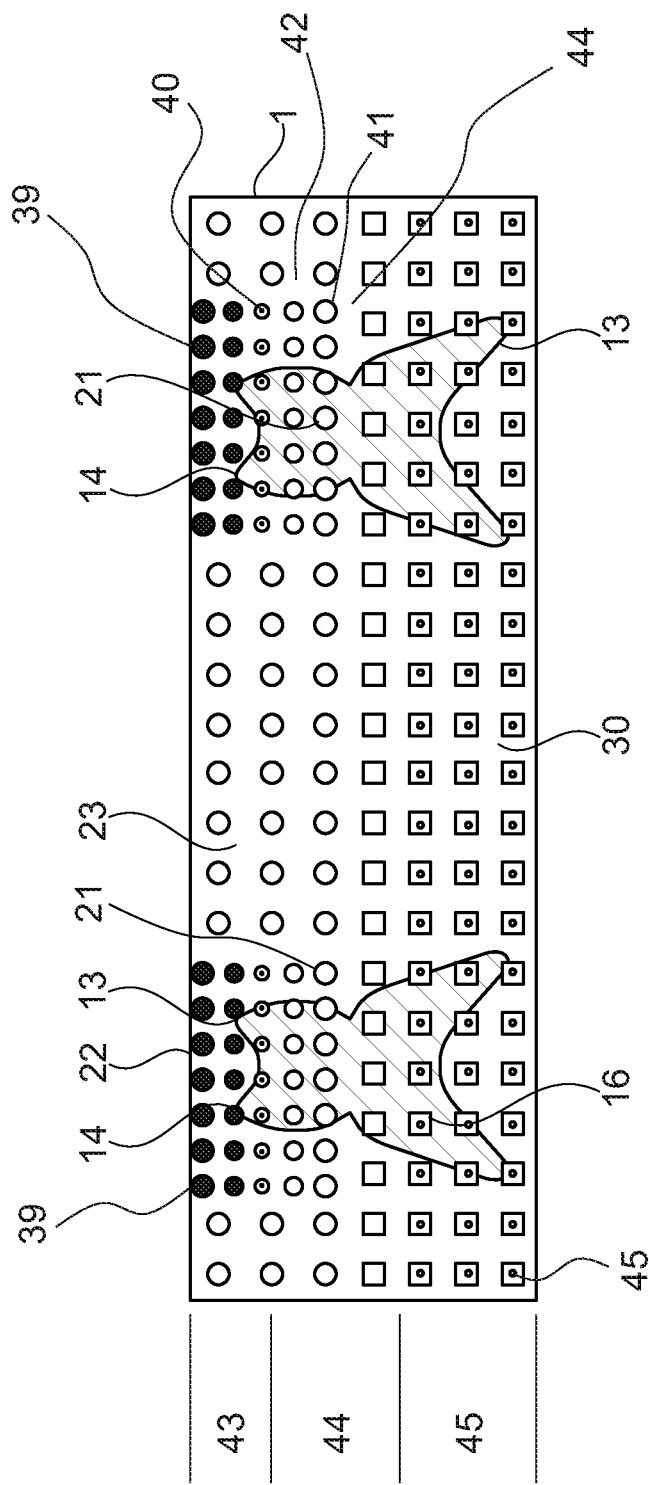

FIG. 10 shows a cross-section of a dried, porous ceramic blank, which has spatially polychromatic, physical zones and a color progression. The color progression of the entire prosthetic body is displayed graphically by the software. The dental technician then determines the desired tooth color progression and the physically important zones of the prosthetic body on his own or on the basis of digital color data. The CAD/CAM system then mills the desired prosthetic body with the corresponding color progression and the corresponding degree of hardness and bending strength values out of the porous ceramic blank.

Figure 11:
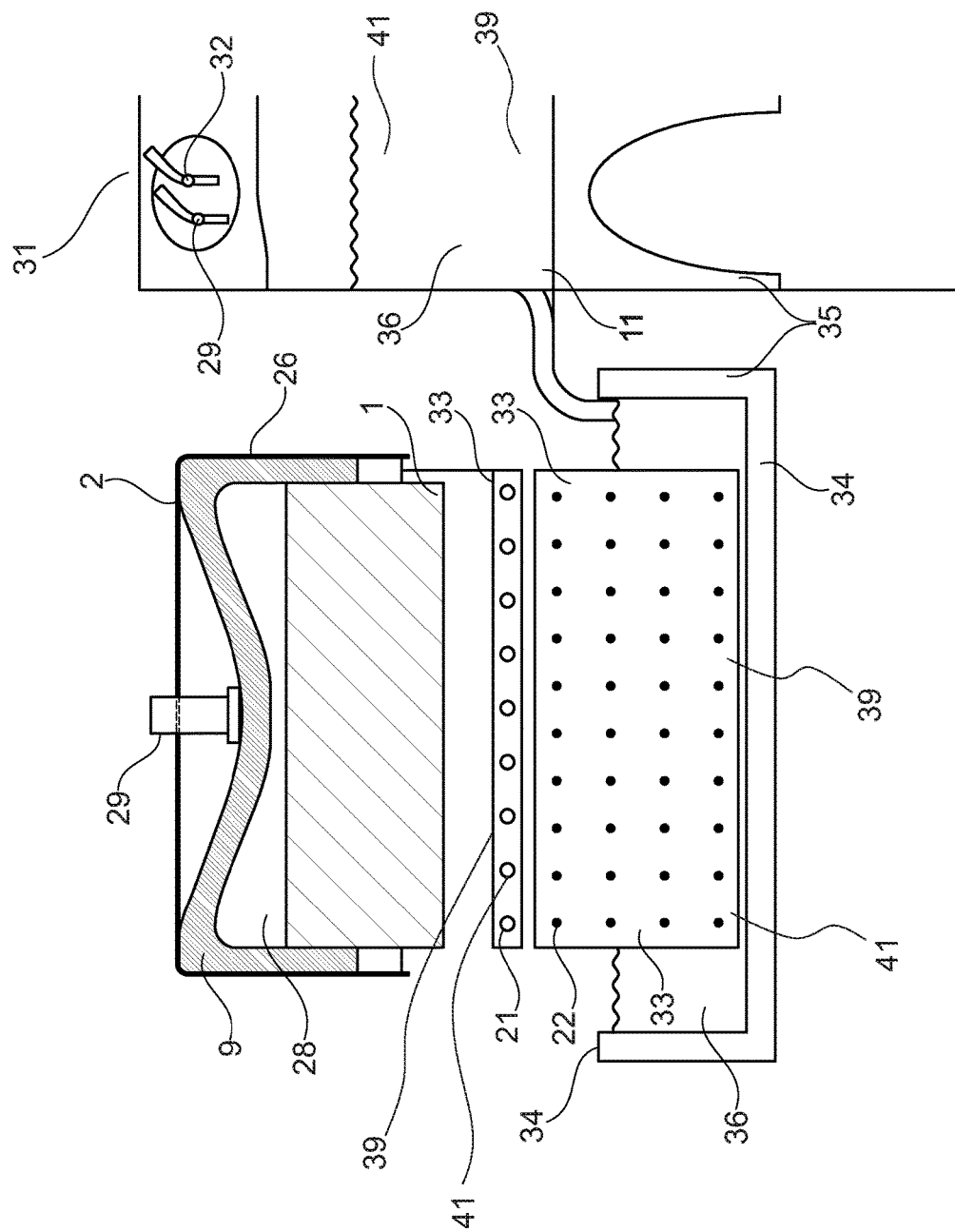

FIG. 11 shows a cross-section of the entire system, comprising a silicone mold housing, porous ceramic blanks (2), interchangeable or layerable loading body materials (33) with possible color components and/or coloring pigment solution and/or coloring pigment stabilizer solution and/or solutions of the chemical stabilizers for the oxide ceramic under capillary pressure (21) (41). FIG. 11 further shows the capillary pressure-retaining device for loading with solvent from a loading body material and the reservoir (7) (made of porous or foam-like materials) with and/or without color-producing components, with an optional capillary pressure controlled equalization tank (31) and with an atmospheric pressure valve and/or a suction pressure application valve (29).

Figure 12:
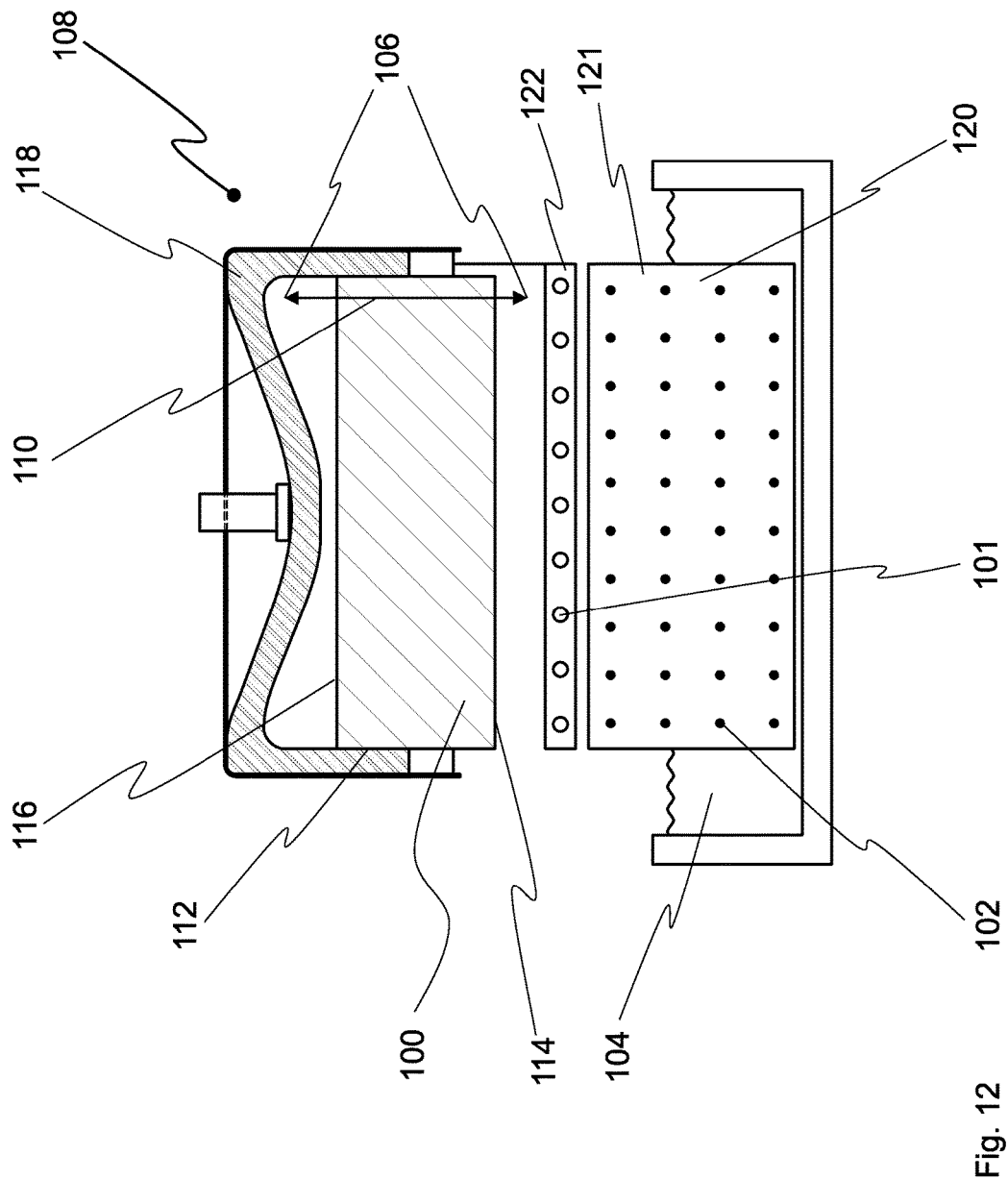

According to FIG. 12, the porous ceramic body 100 is fitted positively into a mold 118, in particular a silicone mold, wherein a freely accessible surface 114 can be placed on a loading body 120 that has two layers 121, 122, for the purpose of loading the ceramic body with chemical substances 101, 102 that are suitable for influencing the physical properties of the porous ceramic body 100 and are contained in a solution 104. With respect to the freely accessible surface 114 and an isolated or sealed surface 116, an ambient parameter gradient 110 between a parameter 105 within the mold 118 and an ambient parameter 106 in a surrounding area 108 can be created by adjusting the ambient parameter 106 and/or by adjusting the parameter 105.

LIST OF REFERENCE SIGNS

1—preparing the porous and/or sintered and/or unbound and/or bound ceramic
2—e.g. silicone mold with porous ceramic blank placed therein,
3—loading the porosities of the ceramic blank, wherein steps 2 and 3 may be carried out in any sequence
4—distribution step of components
5—removal of liquid until the distribution control step in, e.g. the silicone mold is completed
6—drying the porous ceramic blank
7—CAD/CAM processing
8—inner surface of the dental prosthesis and/or the implant or prosthetic implant
9—silicone
10—valve
11—
12—symbol for distribution control step
13—dashed images for planned CAD/CAM processing
14—prosthetic tooth
15—pink colored portion
16—possible incorporation in 3-dimensional color space
17—color components
18—liquid removal
19—air humidity 20—temperature
21—color-producing component concentrations (large)
22—color-producing component concentrations (small)
23—colorless components, e.g. for concentration equalization, large
24—colorless components, e.g. for concentration equalization, small
25—e.g. silicone housing cover frame
26—
27—vessel
28—region under atmospheric pressure or without atmospheric pressure
29—valve triggered under atmospheric pressure
30—tooth color pink gum color
31—capillary pressure controlled equalization tank
32—pressure adjustment valves
33—loading body
34—capillary pressure-retaining device for loading with solvent from a loading body material
35—loading body material solvent reservoir
36—coloring pigment solution
37—stabilizers
38—stabilizers against calcining
39—hardness reducing stabilizers components concentrations (large)
40—hardness reducing stabilizers components concentrations (small)
41—stabilizers and/or color-producing concentrations (large)
42—stabilizers and/or color-producing concentrations (small)
43—zone C=hardness HV of 450 to 1450
44—zone D=flexural strength MPa of 500 to 2000
45—zone E=fracture toughness in MPa/m$^2$ of 5-16
a,b,c,d coloring with gradations from light to dark
110—porous ceramic
101, 102—chemical substances that are suitable for influencing physical properties
104—solution
105—parameter
106—ambient parameter
108—environment
110—ambient parameter gradient
112—isolated and/or sealed part of a surface
114—second freely accessible surface
116—first isolated and/or sealed surface
118—mold
120—loading body
121, 122—layer

The invention claimed is:

1. A process for producing a ceramic body (100), having selectively adjustable degrees of expression of one or more different physical properties, characterized in that the ceramic body (100) has a porosity to enable the control of a selective distribution of one or more chemical substances (101, 102) that are suitable for influencing the physical properties of the ceramic body (100), and in a first step, which is a loading step, the ceramic body is loaded with one or more solutions (104) of the one or more chemical substances (101, 102), and in a second step, which is a distribution step, the distribution of the one or more chemical substances (101, 102) within the porous ceramic body (100) is controlled, wherein a progression or a spatial progression of the degree of expression of the one or more physical properties can be produced and the one or more chemical substances (101, 102) are distributed within the ceramic body (100) by way of a convection flow, and wherein the control is effected by adjusting one or more ambient parameters (106) in an environment (108), and wherein a flow direction and a flow rate are controlled by the selective creation of ambient parameter gradients (110), with respect to various surfaces (116, 114) of the porous ceramic (100).

2. The process according to claim 1, characterized in that a speed of movement of the one or more chemical substances (101, 102) or the flow rate is controlled by increasing or decreasing one or more ambient parameter gradients (110).

3. The process according to claim 1, characterized in that a direction of movement of the one or more chemical substances (101, 102) or the direction of flow is controlled by changing the direction of one or more ambient parameter gradients (110).

4. The process according to claim 1, characterized in that at least one surface (116) or at least one part of a surface (112) of the ceramic body (100) is isolated or sealed off during the loading step or during the distribution control step, and in that at least one other surface (114) or at least one other part of a surface of the ceramic body (100) is freely accessible for loading or for control.

5. The process according to claim 1, characterized by the following steps,
preparing a porous ceramic blank (100),
providing one or more surfaces (112, 116) of the ceramic blank (100) with an isolation or sealing, wherein the ceramic blank is placed in a precise fit inside a fluid-tight/air-impermeable mold (118) in such a way that at least one surface (114) of the ceramic blank (100) is freely accessible,
loading the freely accessible surface (114) of the ceramic blank (100) with one or more chemical substances (101, 102), wherein the one or more chemical substances (101, 102), which are suitable for influencing the physical properties of the ceramic blank (100), are contained in one or more solutions (104),
placing the ceramic blank (100) within an environment (108), the ambient parameters (106) of which are adjustable, wherein the freely accessible surface (114) of the ceramic blank (100) is in contact with the environment (108),
controlling the distribution of the one or more chemical substances (101, 102) within the ceramic blank (100), wherein at least one ambient parameter (106) is adjusted in order to create an ambient parameter gradient (110) between the freely accessible surface (114) and the one or more isolated or sealed off surfaces (112, 116) of the ceramic blank (100).

6. The process according to claim 5, characterized in that the one or more solutions (104) of one or more chemical substances (101, 102) are controlled within the ceramic body (100) in such a way that a concentration of the dissolved chemical substances (101, 102) in different regions of the ceramic body has different values, so that in different regions of the ceramic body (100), different degrees of expression of the physical properties are established.

7. The process according to claim 5, characterized in that the solution (104) comprises distilled water, zirconium nitrate and at least one chemical substance (101, 102) that is suitable for influencing the physical properties of the ceramic body (100).

8. The process according to claim 1, characterized in that a degree of expression of an opacity or a translucency of the ceramic body (100) is controlled by means of an yttrium-containing solution (104).

9. The process according to claim 1, characterized in that a degree of expression of a hardness or a strength or a toughness of the ceramic body (100) is controlled by means of a cerium-containing solution (104).

10. The process according to claim 1, characterized in that a configuration of a crystal system of the ceramic body (100) or of individual regions of the ceramic body (100) is controlled by means of a solution (104) that contains calcium or magnesium or yttrium.

11. The process according to claim 10, characterized in that the crystal system of the ceramic body (100) is stabilized at least regionally in a cubic configuration, wherein the solution (104) contains a mole fraction of at least 16% calcium or 16% magnesium or 8% yttrium.

12. The process according to claim 10, characterized in that the crystal system of the ceramic body (100) is stabilized at least regionally in a tetragonal configuration, wherein the solution (104) contains a mole fraction of at least 8% calcium or 8% magnesium or 4% yttrium.

13. The process according to claim 1, characterized in that a crystal system is stabilized in a cubic or tetragonal configuration within pores of the ceramic body (100) by means of a solution (104) that comprises zirconium nitrate and calcium or magnesium or yttrium.

14. A ceramic blank (100), suitable for producing a dental prosthesis by means of a CAD/CAM milling machine, produced in a process according to claim 1, characterized by a spatial distribution of one or more chemical substances (101, 102) that are suitable for influencing the physical properties of the ceramic blank (100), wherein the spatial distribution of the one or more chemical substances (101, 102) can be controlled by means of ambient parameter gradients (110), and wherein the ceramic blank (100) may be subjected to a heat treatment, in particular a sintering process, for the purpose of adjusting a gradual or graduated progression of the degree of expression of one or more physical properties.

* * * * *